(12) United States Patent
Xu

(10) Patent No.: US 11,684,764 B2
(45) Date of Patent: Jun. 27, 2023

(54) CLOSED-LOOP ACTUATING AND SENSING EPIDERMAL SYSTEMS

(71) Applicant: THE REGENTS OF THE UNIVERSITY OF CALIFORNIA, Oakland, CA (US)

(72) Inventor: Sheng Xu, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 447 days.

(21) Appl. No.: 16/093,820

(22) PCT Filed: Apr. 14, 2017

(86) PCT No.: PCT/US2017/027656
§ 371 (c)(1),
(2) Date: Oct. 15, 2018

(87) PCT Pub. No.: WO2017/181027
PCT Pub. Date: Oct. 19, 2017

(65) Prior Publication Data
US 2019/0388667 A1    Dec. 26, 2019

Related U.S. Application Data

(60) Provisional application No. 62/322,567, filed on Apr. 14, 2016.

(51) Int. Cl.
*A61M 37/00* (2006.01)
*A61N 1/04* (2006.01)
*H05K 1/02* (2006.01)

(52) U.S. Cl.
CPC ....... *A61M 37/0015* (2013.01); *A61N 1/0428* (2013.01); *A61M 2037/0007* (2013.01);
(Continued)

(58) Field of Classification Search
CPC ...... A61M 37/0015; A61M 2037/0023; A61M 2037/0061; A61M 2037/003; A61M 2037/0046; A61M 2205/3303
See application file for complete search history.

(56) References Cited

U.S. PATENT DOCUMENTS

| 7,344,499 B1 | 3/2008 | Prausnitz |
| 2007/0100274 A1 | 5/2007 | Young et al. |

(Continued)

FOREIGN PATENT DOCUMENTS

| WO | 2014/126927 A1 | 8/2014 | |
| WO | WO 2014/124049 | * 8/2014 | ............ H01L 23/18 |
| WO | 2015/184084 A2 | 12/2015 | |

OTHER PUBLICATIONS

D.-H. Kim, J.-H. Ahn, W. M. Choi, H.-S. Kim, T.-H. Kim, J. Song, Y. Y. Huang, Z. Liu, C. Lu, J. A. Rogers, Stretchable and Foldable Silicon Integrated Circuits, Science 320, 507-511 (2008) (21 pages total).

(Continued)

*Primary Examiner* — Emily L Schmidt

(57) ABSTRACT

A closed-loop wearable device or platform integrates sensors, actuators, and microcontroller on board. The device is applied directly to the skin using stretchable epidermal electronics. It can sense a variety of signals from the human body, thus collecting medically relevant information, and can activate delivery of a therapeutic upon detection of an abnormal condition. The therapeutic can be delivered at a personalized dosage and/or with a unique combination of drugs or other agents based on the individual's metabolism as tracked by various sensor modules integrated with the medical device.

16 Claims, 15 Drawing Sheets

(52) U.S. Cl.
CPC ............... *A61M 2037/0023* (2013.01); *A61M 2205/0216* (2013.01); *A61M 2205/3303* (2013.01); *A61M 2205/3368* (2013.01); *A61M 2205/3561* (2013.01); *A61M 2205/70* (2013.01); *A61M 2230/50* (2013.01); *A61M 2230/65* (2013.01); *H05K 1/0283* (2013.01)

(56) References Cited

U.S. PATENT DOCUMENTS

| | | | |
|---|---|---|---|
| 2012/0130207 A1* | 5/2012 | O'Dea | A61M 37/0015 600/309 |
| 2012/0244848 A1* | 9/2012 | Ghaffari | H04M 1/72412 455/575.8 |
| 2013/0041235 A1 | 2/2013 | Rogers | |
| 2013/0140649 A1* | 6/2013 | Rogers | H01L 29/66007 257/414 |
| 2015/0373831 A1 | 12/2015 | Jia et al. | |

OTHER PUBLICATIONS

R. C. Webb, A. P. Bonifas, A. Behnaz, Y. Zhang, K. J. Yu, H. Cheng, M. Shi, Z. Bian, Z. Liu, Y. S. Kim, W. H. Yeo, J. S. Park, J. Song, Y. Li, Y. Huang, A. M. Gorbach, J. A. Rogers, Ultrathin conformal devices for precise and continuous thermal characterization of human skin, Nat Mater 12, 938-944 (2013) (15 pages total).

Y. Hattori, L. Falgout, W. Lee, S. Y. Jung, E. Poon, J. W. Lee, I. Na, A. Geisler, D. Sadhwani, Y. Zhang, Y. Su, X. Wang, Z. Liu, J. Xia, H. Cheng, R. C. Webb, A. P. Bonifas, P. Won, J. W. Jeong, K. I. Jang, Y. M. Song, B. Nardone, M. Nodzenski, J. A. Fan, Y. Huang, D. P. West, A. S. Paller, M. Alam, W. H. Yeo, J. A. Rogers, Multifunctional skin-like electronics for quantitative, clinical monitoring of cutaneous wound healing, Adv Healthc Mater 3, 1597-1607 (2014) (20 pages total).

G. Canavese, S. Stassi, M. Stralla, C. Bignardi, C. F. Pirri, Stretchable and conformable metal-polymer piezoresistive hybrid system, Sensors and Actuators A: Physical 186, 191-197 (2012) (7 pages total).

S. Xu, Y. H. Zhang, J. Cho, J. Lee, X. Huang, L. Jia, J. A. Fan, Y. W. Su, J. Su, H. G. Zhang, H. Y. Cheng, B. W. Lu, C. J. Yu, C. Chuang, T. I. Kim, T. Song, K. Shigeta, S. Kang, C. Dagdeviren, I. Petrov, P. V. Braun, Y. G. Huang, U. Paik, J. A. Rogers, Stretchable batteries with self-similar serpentine interconnects and integrated wireless recharging systems, Nature Communications 4, 1543 (2013) (8 pages total).

M. A. Unger, H.-P. Chou, T. Thorsen, A. Scherer, S. R. Quake, Monolithic Microfabricated Valves and Pumps by Multilayer Soft Lithography, Science 288, 113-116 (2000) (4 pages total).

A. W. Martinez, S. T. Phillips, G. M. Whitesides, E. Carrilho, Diagnostics for the Developing World: Microfluidic Paper-Based Analytical Devices, Analytical Chemistry 82, 3-10 (2010) (8 pages total).

A. W. Martinez, S. T. Phillips, B. J. Wiley, M. Gupta, G. M. Whitesides, Flash: A rapid method for prototyping paper-based microfluidic devices, Lab on a Chip 8, 2146-2150 (2008) (10 pages total).

W. Dungchai, O. Chailapakul, C. S. Henry, Electrochemical Detection for Paper-Based Microfluidics, Analytical Chemistry 81, 5821-5826 (2009) (6 pages total).

S. Wang, M. Li, J. Wu, D.-H. Kim, N. Lu, Y. Su, Z. Kang, Y. Huang, J. A. Rogers, Mechanics of Epidermal Electronics, Journal of Applied Mechanics 79, 03102022-031022 (2012) (6 pages total).

"Report to the president engage to excel: producing one million additional college graduates with degrees in science, technology, engineering, and mathematics" (2012) (130 pages total).

International Search Report and Written Opinion dated Jul. 18, 2017 issued in connection with corresponding International Application No. PCT/US2017/027656 (10 pages total).

J. S. Boateng, K. H. Matthews, H. N. E. Stevens, G. M. Eccleston, Wound healing dressings and drug delivery systems: A review, Journal of Pharmaceutical Sciences 97, 2892-2923 (2008) (32 pages total).

A. J. Singer, R. A. F. Clark, Cutaneous Wound Healing, New England Journal of Medicine 341, 738-746 (1999) (9 pages total).

H. Brem, O. Stojadinovic, R. F. Diegelmann, H. Entero, B. Lee, I. Pastar, M. Golinko, H. Rosenberg, M. Tomic-Canic, Molecular markers in patients with chronic wounds to guide surgical debridement, Mol Med 13, 30-39 (2007) (10 pages total).

R. G. Frykberg, J. Banks, Challenges in the Treatment of Chronic Wounds, Advances in Wound Care 4, 560-582 (2015) (23 pages total).

W. J. Jeffcoate, K. G. Harding, Diabetic foot ulcers, The Lancet 361, 1545-1551 (2003) (7 pages total).

F. Gottrup, P. Holstein, B. Jørgensen, M. Lohmann, T. Karlsmar, A new concept of a multidisciplinary wound healing center and a national expert function of wound healing, Archives of Surgery 136, 765-772 (2001) (8 pages total).

T. Sterken, J. Vanfleteren, T. Torfs, M. op de Beeck, F. Bossuyt, C. Van Hoof, "Ultra-Thin Chip Package (UTCP) and Stretchable Circuit Technologies for Wearable ECG System" in Engineering in Medicine and Biology Society,EMBC, 2011 Annual International Conference of the IEEE. (2011), pp. 6886-6889 (4 pages total).

D.-H. Kim, J. A. Rogers, Stretchable Electronics: Materials Strategies and Devices, Advanced Materials 20, 4887-4892 (2008) (6 pages total).

J. A. Rogers, Y. G. Huang, A curvy, stretchy future for electronics, Proceedings of the National Academy of Sciences of the United States of America 106, 10875-10876 (2009) (3 pages total).

W.-H. Yeo, Y.-S. Kim, J. Lee, A. Ameen, L. Shi, M. Li, S. Wang, R. Ma, S. H. Jin, Z. Kang, Y. Huang, J. A. Rogers, Multifunctional Epidermal Electronics Printed Directly Onto the Skin, Advanced Materials 25, 2773-2778 (2013) (14 pages total).

D. H. Kim, N. S. Lu, R. Ghaffari, Y. S. Kim, S. P. Lee, L. Z. Xu, J. A. Wu, R. H. Kim, J. Z. Song, Z. J. Liu, J. Viventi, B. de Graff, B. Elolampi, M. Mansour, M. J. Slepian, S. Hwang, J. D. Moss, S. M. Won, Y. G. Huang, B. Litt, J. A. Rogers, Materials for multifunctional balloon catheters with capabilities in cardiac electrophysiological mapping and ablation therapy, Nature Materials 10, 316-323 (2011) (15 pages total).

J. J. Jeong, M. K. Kim, H. Y. Cheng, W. H. Yeo, X. Huang, Y. H. Liu, J. B. Lim, Y. H. Zhang, Y. G. Huang, J. A. Rogers, Capacitive epidermal electronics for electrically safe, long-term Electrophysiological Measurements, Advanced Healthcare Materials 3, 642-648 (2013) (7 pages total).

R. C. Webb, A. P. Bonifas, A. Behnaz, Y. Zhang, K. J. Yu, H. Cheng, M. Shi, Z. Bian, Z. Liu, Y.-S. Kim, W.-H. Yeo, J. S. Park, J. Song, Y. Li, Y. Huang, A. M. Gorbach, J. A. Rogers, Ultrathin conformal devices for precise and continuous thermal characterization of human skin, Nature Materials 12, 938-944 (2013) (35 pages total).

D. D. Kamaushenko, D. Kamaushenko, D. Makarov, O. G. Schmidt, Compact helical antenna for smart implant applications, NPG Asia Mater 7, e188 (2015) (10 pages total).

L. Y. Chen, B. C. K. Tee, A. L. Chortos, G. Schwartz, V. Tse, D. J. Lipomi, H. S. P. Wong, M. V. McConnell, Z. Bao, Continuous wireless pressure monitoring and mapping with ultra-small passive sensors for health monitoring and critical care, Nature Communications 5, (2014) (10 pages total).

L. Y. Chen, B. C. K. Tee, A. L. Chortos, G. Schwartz, V. Tse, D. J. Lipomi, H. S. P. Wong, M. V. McConnell, Z. Bao, Continuous wireless pressure monitoring and mapping with ultra-small passive sensors for health monitoring and critical care, Nature Communications 5, (2014) (6 pages total).

T. I. Kim, J. G. McCall, Y. H. Jung, X. Huang, E. R. Siuda, Y. H. Li, J. Z. Song, Y. M. Song, H. A. Pao, R. H. Kim, C. F. Lu, S. D. Lee, I. S. Song, G. Shin, R. Al-Hasani, S. Kim, M. P. Tan, Y. G. Huang, F. G. Omenetto, J. A. Rogers, M. R. Bruchas, Injectable, Cellular-Scale Optoelectronics with Applications for Wireless Optogenetics, Science 340, 211-216 (2013) (6 pages total).

J.-W. Jeong, Jordan G. McCall, G. Shin, Y. Zhang, R. Al-Hasani, M. Kim, S. Li, Joo Y. Sim, K.-I. Jang, Y. Shi, Daniel Y. Hong, Y. Liu, Gavin P. Schmitz, L. Xia, Z. He, P. Gamble, Wilson Z. Ray, Y.

(56) References Cited

OTHER PUBLICATIONS

Huang, Michael R. Bruchas, John A. Rogers, Wireless Optofluidic Systems for Programmable In Vivo Pharmacology and Optogenetics, Cell 162, 662-674 (2015) (14 pages total).

Y. M. Chi, G. Cauwenberghs, "Wireless Non-contact EEG/ECG Electrodes for Body Sensor Networks", in Body Sensor Networks (BSN), 2010 International Conference on. (2010), pp. 297-301 (4 pages total).

B. Xu, A. Akhtar, Y. Liu, H. Chen, W.-H. Yeo, S. Park, II, B. Boyce, H. Kim, J. Yu, H.-Y. Lai, S. Jung, Y. Zhou, J. Kim, S. Cho, Y. Huang, T. Bretl, J. A. Rogers, An Epidermal Stimulation and Sensing Platform for Sensorimotor Prosthetic Control, Management of Lower Back Exertion, and Electrical Muscle Activation, Adv Mater. Jun. 2016 ; 28(22): 4462-4471 (18 pages total).

R. C. Webb, Y. Ma, S. Krishnan, Y. Li, S. Yoon, X. Guo, X. Feng, Y. Shi, M. Seidel, N. H. Cho, J. Kurniawan, J. Ahad, N. Sheth, J. Kim, J. G. Taylor VI, T. Darlington, K. Chang, W. Huang, J. Ayers, A. Gruebele, R. M. Pielak, M. J. Slepian, Y. Huang, A. M. Gorbach, J. A. Rogers, Epidermal devices for noninvasive, precise, and continuous mapping of macrovascular and microvascular blood flow, Science Advances 1, (2015) (13 pages total).

J. Kim, G. Valdes-Ramirez, A. J. Bandodkar, W. Jia, A. G. Martinez, J. Ramirez, P. Mercier, J. Wang, Non-invasive mouthguard biosensor for continuous salivary monitoring of metabolites, Analyst 139, 1632-1636 (2014) (6 pages total).

P. B. Lillehoj, M. C. Huang, C. M. Ho, "A Handheld, Cell Phone-Based Electrochemical Biodetector" in Micro Electro Mechanical Systems (MEMS), 2013 IEEE 26th International Conference on. (2013), pp. 53-56 (4 pages total).

X. Chen, Y. Wang, J. Zhou, W. Yan, X. Li, J.-J. Zhu, Electrochemical Impedance Immunosensor Based on Three-Dimensionally Ordered Macroporous Gold Film, Analytical Chemistry 80, 2133-2140 (2008) (8 pages total).

R. Abraham, S. Buxbaum, J. Link, R. Smith, C. Venti, M. Darsley, Determination of binding constants of diabodies directed against prostate-specific antigen using electrochemiluminescence-based immunoassays, Journal of Molecular Recognition 9, 456-461 (1996) (6 pages total).

B. A. R. Williams, C. W. Diehnelt, P. Belcher, M. Greving, N. W. Woodbury, S. A. Johnston, J. C. Chaput, Creating Protein Affinity Reagents by Combining Peptide Ligands on Synthetic DNA Scaffolds, Journal of the American Chemical Society 131, 17233-17241 (2009) (19 pages).

M. B. Brown, G. P. Martin, S. A. Jones, F. K. Akomeah, Dermal and Transdermal Drug Delivery Systems: Current and Future Prospects, Drug Delivery 13, 175-187 (2006) (13 pages total).

Y.-C. Kim, J.-H. Park, M. R. Prausnitz, Microneedles for drug and vaccine delivery, Advanced Drug Delivery Reviews 64, 1547-1568 (2012) (51 pages total).

B. W. Barry, Novel mechanisms and devices to enable successful transdermal drug delivery, European Journal of Pharmaceutical Sciences 14, 101-114 (2001) (14 pages total).

R. Singh, S. Singh, J. W. Lillard, Past, present, and future technologies for oral delivery of therapeutic proteins, Journal of Pharmaceutical Sciences 97, 2497-2523 (2008) (37 pages total).

M. R. Prausnitz, R. Langer, Transdermal drug delivery, Nature Biotechnology 26, 1261-1268 (2008) (18 pages total).

M. Kaur, K. B. Ita, I. E. Popova, S. J. Parikh, D. A. Bair, Microneedle-assisted delivery of verapamil hydrochloride and amlodipine besylate, European Journal of Pharmaceutics and Biopharmaceutics 86, 284-291 (2014) (8 pages total).

M. Roustit, S. Blaise, J.-L. Cracowski, Trials and tribulations of skin iontophoresis in therapeutics, British Journal of Clinical Pharmacology 77, 63-71 (2014) (9 pages total).

W. G. Lee, U. Demirci, A. Khademhosseini, Microscale electroporation: challenges and perspectives for clinical applications, Integrative Biology 1, 242-251 (2009) (19 pages total).

J. W. Lee, P. Gadiraju, J.-H. Park, M. G. Allen, M. R. Prausnitz, Microsecond thermal ablation of skin for transdermal drug delivery, Journal of Controlled Release 154, 58-68 (2011) (24 pages).

T. Liu, F. Yang, Z. Li, C. Yi, X. Bai, A Prospective Pilot Study to Evaluate Wound Outcomes and Levels of Serum C-reactive Protein and Interleukin-6 in the Wound Fluid of Patients with Trauma-related Chronic Wounds, Ostomy Wound Management 60, 30-37 (2014) (8 pages total).

T. Yang, S. Wang, H. Jin, W. Bao, S. Huang, J. Wang, An electrochemical impedance sensor for the label-free ultrasensitive detection of interleukin-6 antigen, Sensors and Actuators B: Chemical 178, 310-315 (2013) (6 pages total).

R. Lüttge, E. J. W. Berenschot, M. J. d. Boer, D. M. Altpeter, E. X. Vrouwe, A. v. d. Berg, M. Elwenspoek, Integrated Lithographic Molding for Microneedle-Based Devices, Journal of Microelectromechanical Systems 16, 872-884 (2007) (13 pages total).

M. R. Prausnitz, R. Langer, Transdermal drug delivery, Nat Biotech 26, 1261-1268 (2008) (18 pages total).

H. Trommer, R. H. H. Neubert, Overcoming the Stratum Corneum: The Modulation of Skin Penetration, Skin Pharmacology and Physiology 19, 106-121 (2006) (16 pages total).

M. R. Prausnitz, Microneedles for transdermal drug delivery, Advanced Drug Delivery Reviews 56, 581-587 (2004) (7 pages total).

S. H. Bariya, M. C. Gohel, T. A. Mehta, O. P. Sharma, Microneedles: an emerging transdermal drug delivery system, J Pharm Pharmacol 64, 11-29 (2012) (19 pages total).

S. P. Sullivan, D. G. Koutsonanos, M. Del Pilar Martin, J. W. Lee, V. Zarnitsyn, S. O. Choi, N. Murthy, R. W. Compans, I. Skountzou, M. R. Prausnitz, Dissolving polymer microneedle patches for influenza vaccination, Nat Med 16, 915-920 (2010) (16 pages total).

P. M. Wang, M. Cornwell, J. Hill, M. R. Prausnitz, Precise microinjection into skin using hollow microneedles, J Invest Dermatol 126, 1080-1087 (2006) (8 pages total).

R. F. Donnelly, T. R. Singh, M. M. Tunney, D. I. Morrow, P. A. McCarron, C. O'Mahony, A. D. Woolfson, Microneedle arrays allow lower microbial penetration than hypodermic needles in vitro, Pharm Res 26, 2513-2522 (2009)(18 pages total).

T.-N. Chen, D.-S. Wuu, C.-C. Wu, C.-C. Chiang, Y.-P. Chen, R.-H. Horng, Improvements of Permeation Barrier Coatings Using Encapsulated Parylene Interlayers for Flexible Electronic Applications, Plasma Processes and Polymers 4, 180-185 (2007) (6 pages total).

A. Sun, T. Wambach, A. G. Venkatesh, D. A. Hall, in Biomedical Circuits and Systems Conference (BioCAS), 2014 IEEE. (2014), pp. 312-315 (12 pages total).

J. A. Fan, W. H. Yeo, Y. Su, Y. Hattori, W. Lee, S. Y. Jung, Y. Zhang, Z. Liu, H. Cheng, L. Falgout, M. Bajema, T. Coleman, D. Gregoire, R. J. Larsen, Y. Huang, J. A. Rogers, Fractal design concepts for stretchable electronics, Nat Commun 5, 3266 (2014) (8 pages total).

D.-H. Kim, Y.-S. Kim, J. Wu, Z. Liu, J. Song, H.-S. Kim, Y. Y. Huang, K.-C. Hwang, J. A. Rogers, Ultrathin Silicon Circuits With Strain-Isolation Layers and Mesh Layouts for High-Performance Electronics on Fabric, Vinyl, Leather, and Paper, Advanced Materials 21, 3703-3707 (2009) (6 pages total).

Wang et al., "Hollow Polymer Microneedle Array Fabricated by Photolithography Process Combined with Micromolding Techniqu" in Engineering in Medicine and Biology Society, 2009. EMBC 2009. Annual International Conference of the IEEE. (2009), pp. 7026-7029 (4 pages total).

L. K. Branski, G. G. Gauglitz, D. N. Herndon, M. G. Jeschke, "A review of gene and stem cell therapy in cutaneous wound healing", Burns 35, 171-180 (2009) (15 pages total).

F. Gottrup, "A specialized wound-healing center concept: importance of a multidisciplinary department structure and surgical treatment facilities in the treatment of chronic wounds", The American Journal of Surgery 187, S38-S43 (2004) (6 pages total).

P. Mostafalu, S. Amugothu, A. Tamayol, S. Bagherifard, M. Akbari, A. Khademhosseini, S. Sonkusale, "Smart Flexible Wound Dressing with Wireless Drug Delivery",in Biomedical Circuits and Systems Conference (BioCAS), 2015 IEEE. (2015), pp. 422-425 (4 pages total).

D. Son, J. Lee, S. Qiao, R. Ghaffari, J. Kim, J. E. Lee, C. Song, S. J. Kim, D. J. Lee, S. W. Jun, S. Yang, M. Park, J. Shin, K. Do, M. Lee, K. Kang, C. S. Hwang, N. Lu, T. Hyeon, D.-H. Kim, "Mul-

(56) References Cited

OTHER PUBLICATIONS tifunctional wearable devices for diagnosis and therapy of movement disorders", Nature Nanotechnology 9, 397-404 (2014) (8 pages total).
S. Xu, Y. H. Zhang, L. Jia, K. E. Mathewson, K. I. Jang, J. Kim, H. R. Fu, X. Huang, P. Chava, R. H. Wang, S. Bhole, L. Z. Wang, Y. J. Na, Y. Guan, M. Flavin, Z. S. Han, Y. G. Huang, J. A. Rogers, "Soft Microfluidic Assemblies of Sensors, Circuits, and Radios for the Skin", Science 344, 70-74 (2014) (6 pages total).
J. Kim, A. Banks, H. Cheng, Z. Xie, S. Xu, K.-I. Jang, J. W. Lee, Z. Liu, P. Gutruf, X. Huang, P. Wei, F. Liu, K. Li, M. Dalal, R. Ghaffari, X. Feng, Y. Huang, S. Gupta, U. Paik, J. A. Rogers, "Epidermal Electronics with Advanced Capabilities in Near-Field Communication", Small 25, 4761-4767 (2014).
J. Kim, A. Banks, Z. Xie, S. Y. Heo, P. Gutruf, J. W. Lee, S. Xu, K.-I. Jang, F. Liu, G. Brown, J. Choi, J. H. Kim, X. Feng, Y. Huang, U. Paik, J. A. Rogers, "Miniaturized Flexible Electronic Systems with Wireless Power and Near-Field Communication Capabilities", Advanced Functional Materials 25, 4761-4767 (2015) (7 pages total).
K. H. Shin, C. R. Moon, T. H. Lee, C. H. Lim, Y. J. Kim, "Flexible wireless pressure sensor module, Sensors and Actuators", A-Physical 123-24, 30-35 (2005) (6 pages total).
F. Bossuyt, T. Vervust, F. Axisa, J. Vanfleteren, "A New Low Cost, Elastic and Conformable Electronics Technology for Soft and Stretchable Electronic Devices by use of a Stretchable Substrate" in Microelectronics and Packaging Conference, 2009. EMPC 2009. European. (2009), pp. 1-6 (6 pages total).
R. Carta, P. Jourand, B. Hermans, J. Thone, D. Brosteaux, T. Vervust, F. Bossuyt, F. Axisa, J. Vanfleteren, R. Puers, "Design and implementation of advanced systems in a flexible-stretchable technology for biomedical applications, Sensors and Actuators", A-Physical 156, 79-87 (2009) (9 pages total).
J. Jeon, H. Lee, Z. Bao, "Flexible Wireless Temperature Sensors Based on Ni Microparticle-Filled Binary Polymer Composites", Advanced Materials 25, 850-855 (2013) (6 pages total).
M. J. Cima, "Next-generation wearable electronics", Nature Biotechnology 32, 642-643 (2014) (2 pages total).
P. Mostafalu, W. Lenk, M. Dokmeci, B. Ziaie, A. Khademhosseini, S. Sonkusale, "Wireless Flexible Smart Bandage for Continuous Monitoring of Wound Oxygenation" in Biomedical Circuits and Systems Conference (BioCAS), 2014 IEEE. (2014), pp. 456-459 (4 pages total).
A. J. Bandodkar, D. Molinnus, O. Mirza, T. Guinovart, J. R. Windmiller, G. Valdés-Ramírez, F. J. Andrade, M. J. Schöning, J. Wang, "Epidermal tattoo potentiometric sodium sensors with wireless signal transduction for continuous non-invasive sweat monitoring", Biosensors and Bioelectronics 54, 603-609 (2014) (7 pages total).
B. Schazmann, D. Morris, C. Slater, S. Beirne, C. Fay, R. Reuveny, N. Moyna, D. Diamond, "A wearable electrochemical sensor for the real-time measurement of sweat sodium concentration", Analytical Methods 2, 342-348 (2010) (7 pages total).
A. J. Bandodkar, V. W. S. Hung, W. Jia, G. Valdes-Ramirez, J. R. Windmiller, A. G. Martinez, J. Ramirez, G. Chan, K. Kerman, J. Wang, "Tattoo-based potentiometric ion-selective sensors for epidermal pH monitoring", Analyst 138, 123-128 (2013) (6 pages total).
N. Thomas, I. Lähdesmäki, B. A. Parviz, "A contact lens with an integrated lactate sensor", Sensors and Actuators B: Chemical 162, 128-134 (2012) (7 pages total).
S. Iguchi, H. Kudo, T. Saito, M. Ogawa, H. Saito, K. Otsuka, A. Funakubo, K. Mitsubayashi, "A flexible and wearable biosensor for tear glucose measurement", Biomedical Microdevices 9, 603-609 (2007) (7 pages total).
M. H. Faridnia, G. Palleschi, G. J. Lubrano, G. G. Guilbault, "Amperometric biosensor for determination of lactate in sweat", Analytica Chimica Acta 278, 35-40 (1993) (6 pages total).
W. Jia, A. J. Bandodkar, G. Valdés-Ramírez, J. R. Windmiller, Z. Yang, J. Ramírez, G. Chan, J. Wang, "Electrochemical Tattoo Biosensors for Real-Time Noninvasive Lactate Monitoring in Human Perspiralion", Analytical Chemistry 85, 6553-6560 (2013) (8 pages total).
A. G. Venkatesh, A. Sun, H. Brickner, D. Looney, D. A. Hall, E. Aronoff-Spencer, "Yeast dual-affinity biobricks: Progress towards renewable whole-cell biosensors", Biosensors and Bioelectronics 70, 462-468 (2015) (7 pages total).
A. Bhimji, A. A. Zaragoza, L. S. Live, S. O. Kelley, "Electrochemical Enzyme-Linked Immunosorbent Assay Featuring Proximal Reagent Generation: Detection of Human Immunodeficiency Virus Antibodies in Clinical Samples", Analytical Chemistry 85, 6813-6819 (2013) (7 pages total).
M. Xu, X. Luo, J. J. Davis, "The label free picomolar detection of insulin in blood serum", Biosensors and Bioelectronics 39, 21-25 (2013) (5 pages total).
A. Benvidi, N. Rajabzadeh, M. Mazloum-Ardakani, M. M. Heidari, A. Mulchandani, "Simple and label-free electrochemical impedance Amelogenin gene hybridization biosensing based on reduced graphene oxide", Biosensors and Bioelectronics 58, 145-152 (2014) (8 pages total).
R. Ohno, H. Ohnuki, H. Wang, T. Yokoyama, H. Endo, D. Tsuya, M. Izumi, "Electrochemical impedance spectroscopy biosensor with interdigitated electrode for detection of human immunoglobulin" A, Biosensors and Bioelectronics 40, 422-426 (2013) (5 pages total).
T. Bryan, X. Luo, P. R. Bueno, J. J. Davis, An optimised electrochemical biosensor for the label-free detection of C-reactive protein in blood, Biosensors and Bioelectronics 39, 94-98 (2013) (5 pages total).
N. S. Ferreira, M. G. F. Sales, "Disposable immunosensor using a simple method for oriented antibody immobilization for label-free real-time detection of an oxidative stress biomarker implicated in cancer diseases", Biosensors and Bioelectronics 53, 193-199 (2014) (7 pages total).
W. Su, M. Lin, H. Lee, M. Cho, W.-S. Choe, Y. Lee, "Determination of endotoxin through an aptamer-based impedance biosensor", Biosensors and Bioelectronics 32, 32-36 (2012) (5 pages total).
I. Palchetti, M. Mascini, "Electrochemical nanomaterial-based nucleic acid aptasensors", Analytical and Bioanalytical Chemistry 402, 3103-3114 (2012) (12 pages total).
E. L. Giudice, J. D. Campbell, "Needle-free vaccine delivery", Advanced Drug Delivery Reviews 58, 68-89 (2006) (22 pages total).
J.-P. Amorij, W. L. J. Hinrichs, H. W. Frijlink, J. C. Wilschut, A. Huckriede, "Needle-free influenza vaccination", The Lancet Infectious Diseases 10, 699-711 (2010) (13 pages total).
S. Mitragotri, "Immunization without needles", Nature Reviews: Immunology 5, 905-916 (2005) (12 pages total).
J. T. La Belle, K. Bhavsar, A. Fairchild, A. Das, J. Sweeney, T. L. Alford, J. Wang, V. P. Bhavanandan, L. Joshi, A cytokine immunosensor for multiple sclerosis detection based upon label-free electrochemical impedance spectroscopy, Biosensors and Bioelectronics 23, 428-431 (2007) (4 pages total).
H. Hennessey, N. Afara, S. Omanovic, A. L. Padjen, "Electrochemical investigations of the interaction of C-reactive protein (CRP) with a CRP antibody chemically immobilized on a gold surface", Analytica Chimica Acta 643, 45-53 (2009) (9 pages total).
I. Ciani, H. Schulze, D. K. Corrigan, G. Henihan, G. Giraud, J. G. Terry, A. J. Walton, R. Pethig, P. Ghazal, J. Crain, C. J. Campbell, T. T. Bachmann, A. R. Mount, "Development of immunosensors for direct detection of three wound infection biomarkers at point of care using electrochemical impedance spectroscopy", Biosensors and Bioelectronics 31, 413-418 (2012) (6 pages total).
B. P. Chaudhri, F. Ceyssens, H. P. Neves, A. La Manna, C. Van Hoof, R. Puers, "Out-of-Plane, High strength, Polymer Microneedles for Transdermal Drug Delivery" in Engineering in Medicine and Biology Society, EMBC, 2011 Annual International Conference of the IEEE. (2011), pp. 3680-3683 (4 pages total).
P. Griss, H. Andersson, G. Stemme, "Expandable microspheres for the handling of liquids", Lab Chip 2, 117-120 (2002) (4 pages total).
N. Roxhed, S. Rydholm, B. Samel, W. v. d. Wijngaart, P. Griss, G. Stemme, "A compact, low-cost microliter-range liquid dispenser based on expandable microspheres", Journal of Micromechanics and Microengineering 16, 2740-2746 (2006) (8 pages total).

(56) References Cited

OTHER PUBLICATIONS

H. Kuroki, H. Ohashi, T. Ito, T. Tamaki, T. Yamaguchi, "Isolation and analysis of a grafted polymer onto a straight cylindrical pore in a thermal-responsive gating membrane and elucidation of its permeation behavior", Journal of Membrane Science 352, 22-31 (2010) (10 pages total).

F. Tomicki, D. Krix, H. Nienhaus, M. Ulbricht, "Stimuli-responsive track-etched membranes via surface-initiated controlled radical polymerization: Influence of grafting density and pore size", Journal of Membrane Science 377, 124-133 (2011) (10 pages total).

M. A. M. E. Vertommen, H.-J. L. Cornelissen, C. H. J. T. Dietz, R. Hoogenboom, M. F. Kemmere, J. T. F. Keurentjes, "Pore-covered thermoresponsive membranes for repeated on-demand drug release", Journal of Membrane Science 322, 243-248 (2008) (6 pages total).

I. Lokuge, X. Wang, P. W. Bohn, "Temperature-controlled flow switching in nanocapillary array membranes mediated by poly(N-isopropylacrylamide) polymer brushes grafted by atom transfer radical polymerization", Langmuir 23, 305-311 (2007) (7 pages total).

E. Boireau-Adamezyk, A. Baillet-Guffroy, G. N. Stamatas, "Age-dependent changes in stratum corneum barrier Function", Skin Research and Technology 20, 409-415 (2014) (7 pages total).

W. D. Niles, P. J. Coassin, "Cyclic olefin polymers: innovative materials for high-density multiwell plates", Assay Drug Dev Technol 6, 577-590 (2008) (14 pages total).

Y. Lei, Y. Liu, W. Wang, W. Wu, Z. Li, "Studies on Parylene C-caulked PDMS (pcPDMS) for low permeability required microfluidics applications", Lab Chip 11, 1385-1388 (2011) (4 pages total).

P. Nunes, P. Ohlsson, O. Ordeig, J. Kutter, "Cyclic olefin polymers: emerging materials for lab-on-a-chip applications", Microfluidics and Nanofluidics 9, 145-161 (2010) (17 pages total).

T. Thorsen, S. J. Maerkl, S. R. Quake, "Microfluidic Large-Scale Integration", Science 298, 580-584 (2002) (6 pages total).

J. W. Hong, S. R. Quake, "Integrated nanoliter systems", Nature Biotechnology 21, 1179-1183 (2003) (5 pages total).

W. H. Yeo, Y. S. Kim, J. Lee, A. Ameen, L. Shi, M. Li, S. Wang, R. Ma, S. H. Jin, Z. Kang, Y. Huang, J. A. Rogers, "Multifunctional epidermal electronics printed directly onto the skin", Adv Mater 25, 2773-2778 (2013) (6 pages total).

Wang et al., "Fabrication and Characterization of Polymer Hollow Microneedle Array Using UV Lithography Into Micromolds", Microelectromechanical Systems, Journal of 22, 1041-1053 (2013) (13 pages total).

* cited by examiner

MEMBRANE CLOSE STATE

CLOSED-LOOP ACTUATING AND SENSING EPIDERMAL SYSTEMS

CROSS-REFERENCE TO RELATED APPLICATIONS

This application claims benefit of priority of U.S. Provisional Patent Application Ser. No. 62/322,567, filed Apr. 14, 2016, entitled "WEARABLE "CASES": CLOSED-LOOP ACTUATING AND SENSING EPIDERMAL SYSTEMS", owned by the assignee of the present application and herein incorporated by reference in its entirety.

FIELD

The invention relates to wearable devices for monitoring and delivering therapy.

BACKGROUND

Conventional wearable electronic systems are rigid and planar. They typically involve small numbers of point contacts, flat electrode pads that affix to the soft, curvilinear, and time-dynamic skin with adhesive tapes and often use conductive gels to minimize contact impedances. Examples include metal-plate electrode, microelectrode, intra-cavitary and intra-tissue electrodes (8). These suffer from either unwanted signals due to changes in the electrode-electrolyte interface or high impedance or pain and potential inflammation, respectively. This type of approach, as well as related ones that eliminate the gel, have strong clinical utility for biopotential recording but limited value in everyday life due to irritating discomfort and loss of adhesion that arise from the unfavorable nature of the skin/electrode interface. As a result, existing options in system design are unable to effectively accommodate integration with the soft, textured, curvilinear and time-dynamic surfaces of the skin.

Moreover, these wearable devices still either need to be tethered by cables to the external bulky equipment that synchronize the functionalities of the sensors and actuators or contain non-flexible and rigid surfaces that cannot completely conform to the skin. This requirement severely limits the wearability and mobility of the system, and is therefore of limited practical use.

A promising alternative are stretchable/flexible electronics that can achieve intimate, conformal integration with tissues and organs with minimal mobility confinement and user discomfort. With robust, intimate and low impedance contact, soft devices can eliminate the ever-changing parasitic capacitance at the electrode-body interface, and thus ensure highly sensitive and accurate measurement of electrophysiological signals. This new class of soft electronic devices are therefore of continuing interest for clinical applications such as mobile healthcare, due to their versatile capabilities in noninvasive and physiological diagnostics/prognostics.

Equipped with a variety of not only physical sensors, but also molecular sensors, wearable devices can achieve multi-channel acquisition of different physiological signals and other vital signs regarding the status of human health, augmenting signals such as temperature and acceleration with more diagnostically telling levels of cytokines, metabolites, pH, moisture, etc.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways. In particular, the proposed approach overcomes these drawbacks by coordinating the sensor and actuator modules with on-board data analysis, forming a closed-loop sensing and actuating wearable and modular platform all of which are on stretchable substrates. The wearable device can sense a variety of signals from the human body. Once an abnormal signal is detected, the onboard microcontroller can activate the drug delivery device to cure the abnormal symptoms, forming a closed loop wearable device Existing wearable devices are individual sensors, or individual actuators, or combine sensors and actuators through the external equipment via connection cables. Systems and methods according to present principles has sensors, actuators, and a microcontroller onboard.

Systems and methods according to present principles focus on integrating electrophysiological sensors, drug releasing components, and a controller on an epidermal platform. The sensors can continuously collect vital signs from the human body on a 24/7 basis, which are analyzed and processed locally. In case of abnormal signals, the sensors can trigger release from a drug storage reservoir. The drug releasing may continue until the vital signs return to a normal level or the prescribed dosage has been dispensed. This approach is unique and of practical use as a closed loop system offers the fastest response time. The proposed platform is expandable to collect not only temperature and biomarker measurements, but also other physical/chemical human-health relevant parameters such as local field potentials, acceleration, strain/pressure, pH, toxins, etc. The actuation approach is not limited to pharmaceuticals, but may also perform localized heating/cooling, electrical stimulation, or mechanical massage, among others. The compact, flexible form factor of this device offers robust, yet non-irritating skin/electrode contact. Furthermore, when equipped with wireless data transfer components, the system can be integrated with body-area-networks (BAN) to communicate with an externally functionally expansive central processing unit worn or placed on/in the human body to achieve all-around multi-position health monitoring and treatment. The results can provide a universally adaptable protocol of acquiring electrophysiological signals from the human body, processing data onsite, and delivering corresponding alleviation mechanisms, which may consequently impact the health and wellness of everyday livelihood of the general population.

Advantages of the invention may include, in certain embodiments, one or more of the following. Systems and methods according to present principles allow long-term continuous "24/7" health monitoring and therapy. Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

DETAILED DESCRIPTION

Figure 1:
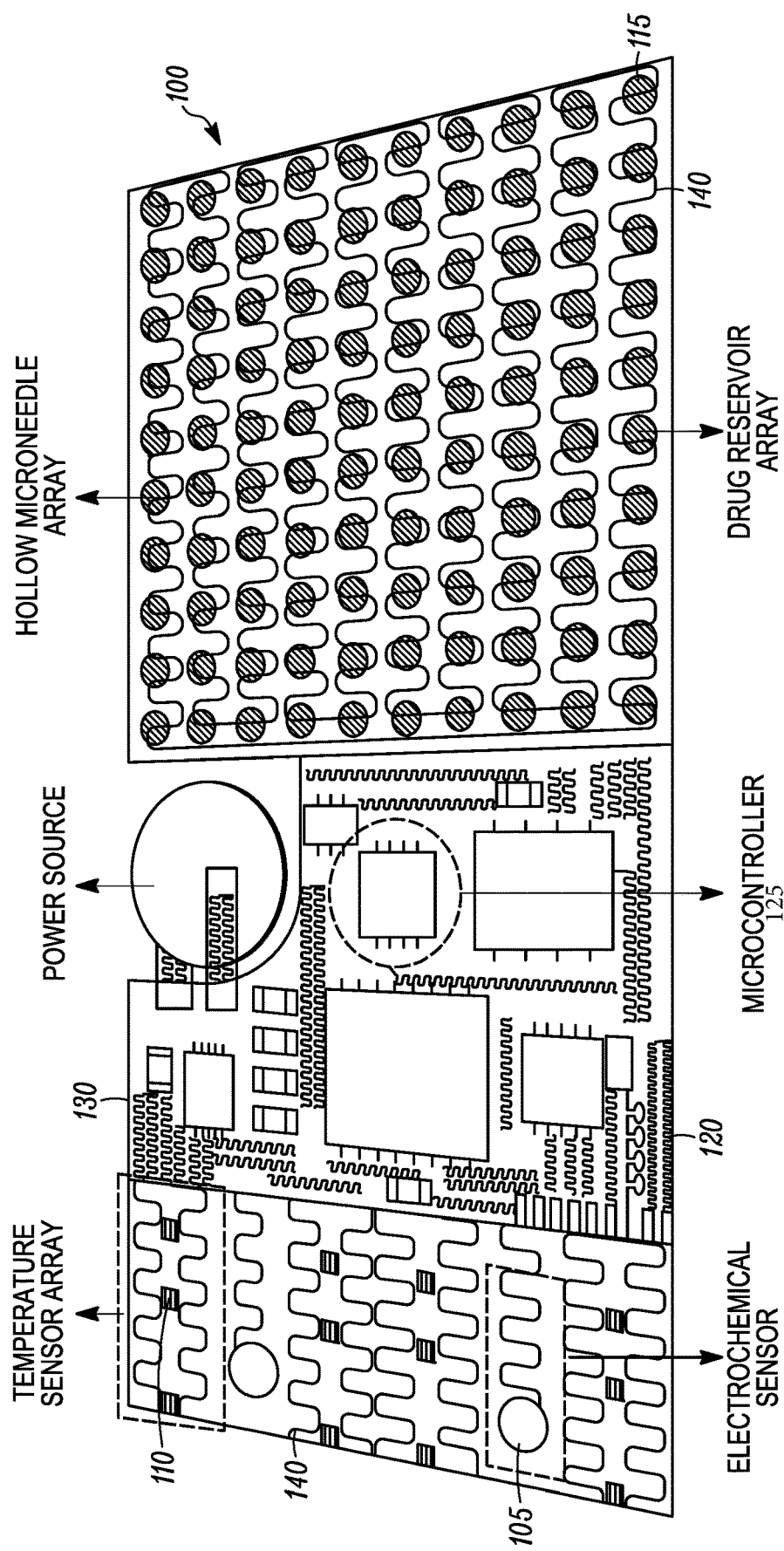
FIG. 1 shows one example of a closed-loop wearable platform or device that integrates electrochemical sensors, temperature sensors, drug delivery devices and a control system on a common substrate.

Disclosed are materials, devices, systems and methods that pertain to a closed-loop wearable platform that integrates sensors, actuators, and microcontroller on board. The system may be applied directly to the skin using stretchable epidermal electronics. It can sense a variety of signals from the human body, thus collecting medically relevant information, and can activate delivery of a therapeutic upon detection of an "abnormal" condition. The therapeutic can be delivered at a personalized dosage or uniquely catered combination of medicines based on the individual's metabolism as tracked by many sensor modules.

Systems and methods according to present principles work by putting closed loop sensing and drug delivery electronics directly on the skin. In this way, conditions can be actively monitored and appropriately treated to speed up healing, reducing the overall cost and patient suffering. Furthermore, these wearable closed loop devices are also able to collect medically relevant information, as opposed to wrist mounted electronics that can provide fitness data but cannot measure other health information accurately enough to be diagnostically relevant. With this meaningful data collection, the proposed closed loop drug delivery system could be further extended to a wide range of pharmaceuticals, where a personalized dosage or unique combination of medicines can be delivered based on individual metabolism as tracked by many sensor modules. This approach involving stretchable epidermal electronics opens up opportunities to develop a new type of wearable, noninvasive and intelligent health cared devices. The mechanical properties of these devices are qualitatively different from those achievable with solid constructs explored previously. By coordinating the sensors and actuators with an onboard processor, the wearable system forms a sensing and curing loop, working without any external intervention. This strategy represents the first step toward of intelligent wearable healthcare system that acts upon the acquired physiological condition of the patient automatically and autonomously.

Systems and methods according to present principles build upon strengths in designing wearable healthcare devices and point-of-care biosensor circuits, and integrate diagnostics, data processing, and therapeutic functionalities onto the same platform not only for tracking wound healing and post-surgery monitoring, but also for administering automated and appropriate drug treatment. Each individual component, such as electrochemical/temperature sensors, transdermal drug delivery systems, and a microcontroller circuit, is fabricated in stretchable formats by advanced microfabrication and materials design, and then assembled together by novel releasable connectors. The resulting system is a wearable smart device similar to a bandage, but which can continuously monitor wound healing, analyze the acquired temperature and biomarker concentration data locally, and trigger actuation such as drug delivery as needed in a timely manner under abnormal situations.

The resulting devices laminate and adhere directly on the skin via van der Waals forces alone and can naturally deform with the skin. In one embodiment the effective modulus of the overall system is only 3-5% higher than the bare soft substrate itself. Through this process, a wearable multifunctional electronic system has been demonstrated with reversible stretchability up to 100%. In some embodiments the device is capable of wireless charging, multi-channel biological signal (e.g. multiple electrophysiological potentials (EP), temperature and acceleration) sensing, and RF communication to a backend receiver. In some cases the overall power consumption of the device may be about 34 mW, and is achieved using resonant inductive coupling. Using a similar approach on the device level, a Li-ion battery with stretchability up to 300% has been demonstrated. The resulting system has a modulus matching that of the human skin so that the user hardly notices it when wearing.

Equipped with a variety of chemical/physical sensor modules, wearable devices can achieve multi-channel acquisition of different physiological signals regarding the status of human health. Even though some conventional devices have integrated actuating capabilities such as electrical stimulation, thermal heating, and drug delivery functions together with the sensors, these wearable devices still need to be tethered by cables to the external bulky equipment that synchronizes the functionalities of the sensors and actuators. This requirement severely limits the wearability and mobility of the system, and is therefore of limited practical use in normal daily life. The wearable devices described herein overcome these limitations by coordinating the sensor and actuator modules with an on-board microcontroller, forming a closed-loop sensing and curing wearable system. The sensors collect the relevant electrophysiological data that is then fed into the pre-programmed microcontroller where the data is analyzed and processed. The microcontroller can send timely commands as needed to regulate the operation of actuators in cases when emergent abnormal signals are detected.

In more detail, through the tracking of biomarkers excreted from the epidermis, either by sweat or open wounds, the skin becomes a significant and noninvasive window into a person's health. However, currently, there is a lack of standard methods that allow for both continuous monitoring of health and rapid, automatic, and appropriate drug delivery via the skin, often crucial in the case of chronic wounds, which take a significant amount of time to heal and frequently reoccur if untreated. Chronic wounds, common among the elderly and those with vascular disease or diabetes, affect approximately 6.5 million in the U.S. and cost an estimated $25 billion annually to treat. Furthermore, complications from diabetic foot ulcers, a specific type of chronic wound, remain the leading cause of amputations worldwide. In developed countries, it has been estimated that 1 to 2% of the population experiences at least one chronic wound during their lifetime. In the Scandinavian countries, the associated costs account for 2-4% of the total health care expenses.

Considering the critical issues an economic loss from chronic wounds, research on chronic wound care is highly demanded to achieve timely and adequate intervention. Hence, by putting closed-loop sensing and drug delivery electronics directly on the skin, these conditions can be actively monitored and appropriately treated to speed up healing reducing the overall cost and patient suffering. Furthermore, these wearable closed-loop devices will also be able to collect medically relevant information, as opposed to wrist-mounted electronics that can provide fitness data but cannot measure other health information accurately enough to be diagnostically relevant. With this meaningful data collection, the closed-looped drug delivery system integrated into a wearable device can be further extended to deliver a wide range of pharmaceuticals, where a personalized dosage or uniquely catered combination of medicines can be delivered based on individual metabolism as tracked by many sensor modules. This approach to stretchable epidermal electronics opens up opportunities to develop a new type of wearable, non-invasive and intelligent healthcare device. The resulting devices have mechanical properties that are qualitatively different from those achievable with solid constructs explored previously. By coordinating the sensors and actuators with an on-board processor, the wearable system forms a sensing-and-curing loop, working without any external intervention. This strategy represents the first step toward an intelligent wearable healthcare system that acts upon the acquired physiological condition of the patient automatically and autonomously.

FIG. 1 shows one example of a closed-loop wearable platform or device 100 that integrates electrochemical sensors 105, temperature sensors 110, drug delivery devices 115 and a control system 120 on a common substrate 130. More generally, the wearable platform 100 may integrate any type of biosensors and actuators (e.g., for drug delivery, heat, electrical and/or pressure stimulation, etc.) with a control system. The electrical interconnects 140 that connect the various components may be formed from metal conductor ribbons, which in the embodiments shown in FIG. 1 has a self-similar serpentine design that allows in-plane and out-of-plane buckling of the structure. The metal conductor ribbons may be sandwiched between two layers of elastomer to further enhance their mechanical robustness. To facilitate the unraveling of the serpentine interconnects, the whole system may be enclosed in a low-damping-coefficient microfluidic environment. The fluid can penetrate between the interconnect structure and the substrate by capillary forces, and perform as a lubricant to facilitate the gliding of the interconnects during the stretching and releasing processes. This interconnect structure provides a hierarchical buckling mechanics and enables the metal structure to sustain a large range of elastic strain and at the same time maintain larger surface area coverage of active device components.

In one embodiment the substrate 130 on which the components are integrated has an elastic stretchability that closely matches human skin. For example, the substrate 130 may be formed from an elastomer material that is able to be stretched or deformed and returned to its original shape without substantial permanant deformation. Such elastomer materials typically undergo elastic deformation. Illustrative elastomers may be formed from polymers, copolymers, composite materials or mixtures of polymers and copolymers. One example of a particular elastomer that may be employed is a silicone elastomer known by the tradename Ecoflex®, which is available from Smooth-On, Inc.

When laminated together and placed on the skin, the microcontroller 125 incorporated in the control system 120 functions as a hub with releasable interconnectors compatible with different sensing modules. Sensors collect the electrophysiological data that is then fed into the microcontroller 125 where the data is analyzed and processed. After which, timely commands are sent to regulate the actuators if and when emergent abnormal signals are detected. The underlying principle is that by monitoring the wound and controlling the amount of therapy (e.g., a drug), treatment outcomes can be improved, particularly in high-risk patients, thereby providing critical capabilities to the healthcare ecosystem.

Figure 2:
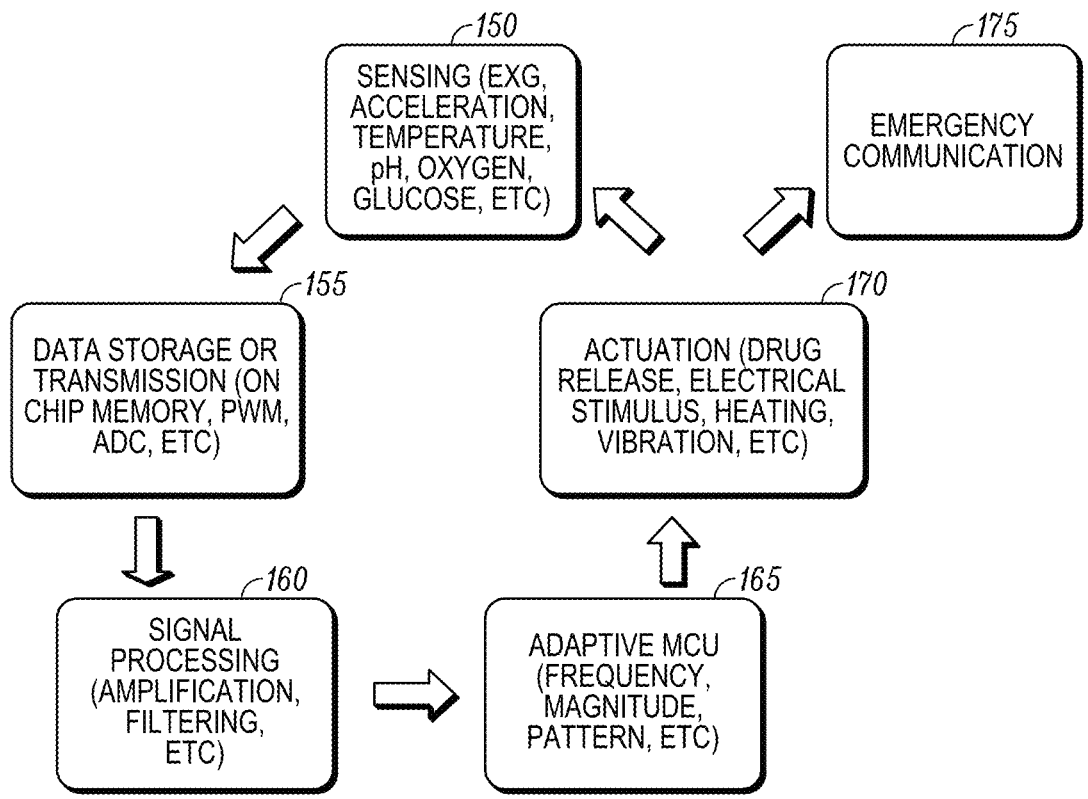
FIG. 2 is a flowchart illustrating one example of the overall operation of the closed-loop wearable platform shown in FIG. 1.

FIG. 2 is a flowchart illustrating one example of the overall operation of the closed-loop wearable platform shown in FIG. 1. As shown, the process begins when the sensors detect any of a variety of different biological and environmental parameters. Next, the data is stored in an on-board memory storage device that is included with the control system. The control system then performs any necessary signal processing and microprocessor control unit in the control system determines the appropriate signal(s) that is to be applied to the actuator(s), or in some cases, determine that that an emergency message should be sent to obtain immediate medical assistance.

In one embodiment, sensors and circuits for use in wearable device that are employed for continuous physiological monitoring may be found in *Skin Soft Microfluidic Assemblies of Sensors, Circuits, and Radios for the Skin*, Science 344, 70 (2014); Sheng Xu et al. Science 344, 70 (2014), which is hereby incorporated by reference in its entirety. In addition, various aspects of examples of circuitry and interconnects that may be employed in the wearable device described herein may be found in U.S. patent application Ser. No. 14/766,301 and Xu S. et al., *Stretchable Batteries With Self-Similar Serpentine Interconnects And Integrated Wireless Recharging Systems*, Nature Communications, 4:1543 doi: 10.1038/ncomms2553 (2013), which are also hereby incorporated by reference in their entirety.

Actuators

The closed-loop wearable devices described herein enable integration of feedback and therapies into passive monitoring. These devices are able to sense stimuli from the environment and react to them by integration of actuation functionalities in the device structure. Identification of problems makes sense only when followed by an adequate actuation that is provided on demand or as a result of detection of an abnormal trend. Providing direct feedback to its wearer, it should improve the patient's awareness and potentially allow better control of his own condition. This actuation may consist of reporting or calling for help, but may also include physical treatment in the event of an emergency.

A variety of different physical treatments may be performed by the actuators incorporated in the closed-loop wearable platform, including any combination of mechanical, thermal, electrical, and chemical treatments. Mechanical treatments may involve artificial muscles, massage and pressure bandages. Thermal treatments may include both heating and cooling.

Electrical treatments may include electrical stimulation, which has been widely used for gentle massage, rehabilitation from disorders of the body, physiotherapy of various types of diseases, or non-pharmacological, non-invasive, quick and easy targeted pain relief, such as in the lower back or abdominal muscles, which has been proven effective for a variety of conditions. Skin mounted thin electrodes are usually utilized for nerve stimulation. One typical example of the electrotherapeutic device is the transcutaneous electrical nerve stimulation device. Electricity is applied to the intact skin through electrodes, which can activate different fibers and eventually reduce the transmission of pain signals from the low contact impedance.

Chemical treatment may involve the controlled delivery of chemicals, such as drugs, growth factors, and neurotransmitters. These treatments may be customized for the individual patent to well match the physiologic rehabilitation processes, thereby increasing effectiveness and minimizing toxic effects. In addition, delivery through the skin bypasses the liver, making it possible to lower drug doses in comparison with oral delivery. Various examples of mechanisms for chemical delivery of drugs and other agents will be presented below.

Drug Delivery Devices

As previously mentioned, a wide variety of different drug delivery devices and other actuators may be incorporated into the closed-loop wearable platform described herein. In this way active actuation functionality is provided on the same flexible/stretchable platform as the sensors on control system. As such, the device can provide timely intervention, such as when the early signs of an infection are detected. As discussed above, the types of actuators that may be employed to provide therapeutic treatment to a patient can take many forms, varying from those that involve direct electrical/thermal stimulation of the tissue/nerves to the aforementioned drug delivery systems, possibly with the integration of microelectromechanical system components. A number of illustrative examples of such actuators will be discussed below.

One of the most important functions of skin is its ability to act as a protective barrier against the ingress of foreign material (chemicals, microbes) and the loss of excessive endogenous material such as water. One class of drug delivery devices that may be employed are referred to as transdermal drug delivery systems (TDDS), which are systems that allow a solute to diffuse through the various layers of skin and into the systemic circulation to thereby cause a therapeutic effect. TDDS have been extensively investigated since the 1990s, and have vied with oral route as the most successful innovative research in drug delivery.

Transdermal drug delivery has two main limitations: transport and dose. Transport is limited by diffusion through the stratum corneum, the ~10 μm thick outermost layer of the skin composed primarily of dead keratinocytes surrounded by a lipid-rich extracellular matrix. This tissue functions to keep things out of the body and poses a formidable barrier to transport of drugs through the skin. The dose and release patterns are to a great extent determined by the combination of guest and the host or the carrier material. Two types of drug delivery mechanisms may be used: a flexible micropump integrated with a painless flexible microneedle fabricated by a lab-on-chip technique, and drug diffusion using silica nanoparticles with a drug into a skin as a transdermal drug delivery. For the former, the micropump can be used for transdermal drug delivery by filling the drug into a reservoir. Hermetic sealing of each reservoir and a reliable means to protect and expose the contents of each reservoir on command are required. For the latter, the diffusion rate of the drug into the skin can be controlled by the temperature, which can be tuned by an integrated microheater.

Figure 3:
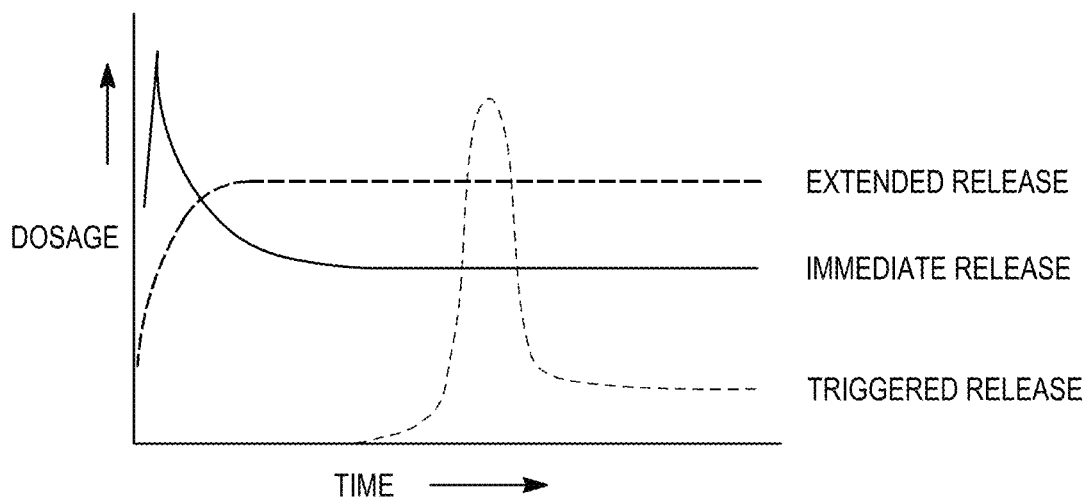
FIG. 3 illustrates various drug release profiles can be used by a drug delivery device in a wearable drug delivery systems.

In general a few typical different types of release profile can be used in wearable drug delivery systems; immediate release, extended release and triggered or delayed release. The different mechanisms are illustrated schematically in FIG. 3. In immediate release formulations, the drugs are available within a relatively short time. Initially the concentration increases rapidly, followed by a sharp decline. Often a relatively high concentration is necessary to achieve the desired effect. This type of release is required in situations where immediate action is essential. In extended release, sometimes called prolonged or sustained release, the availability of drugs is maintained at a lower concentration and for a prolonged time compared to immediate release systems. In extended release systems the drug is delivered at a slow rate and for a prolonged period of time. Different principles are used to control the rate in extended release systems, such as diffusion, decomplexation, dissolution, ion exchange, erosion and degradation. The release of drugs from triggered or delayed release systems is determined by an (external) trigger/stimulus or time. The resulting release can be of the immediate type or slow-release type, depending on the design and the materials chosen. The degree and rate of erosion, degradation or dissolution are, apart from the matrix, a function of, e.g., pH, temperature, ionic strength, or even light and this determines time delay in delayed release systems. The release of the drug from the delivery system might also be triggered by a specific event, situation, or change in the environment. Triggered release systems control drug dosage autonomously over an extended period of time, thus enabling precise dosage levels or more complicated dosage patterns.

Table 1 shows different types of TDDS. Currently most bio-therapeutics and vaccines are injected using a hypodermic needle. However hypodermic needles cannot be easily used by patients themselves and are therefore utilized primarily in the clinics or at home by patients who have received special training on correct injection methods, safe needle disposal, and other issues. Oral drug delivery is another widely used method, but many drugs cannot be given by this route due to poor absorption and drug degradation in the gastrointestinal tract and liver. Other routes of administration have also been investigated, but none offer the broad effectiveness of direct injection using a needle. Among transdermal delivery systems microneedles are one of the most promising, due to their versatility and ability to transfer macromolecules, including therapeutic proteins and vaccines, across the skin. Microneedles puncture the stratum corneum (SC), which consists of dead cells, causing minimal or no pain, and they target their affects only to the SC without harming the deeper tissues. One type of microneedle that may be employed are hollow microneedles (HMN) provide controllable delivery by changing pressure, and thereby flow rate for a rapid bolus injection, a slow infusion, or a varied delivery rate. HMNs selectively permeabilize the SC by creating micron sized pores in the skin to enhance the drug delivery. Microneedles are ideal for patients as they do not stimulate nerves that are associated with pain. Patients with needle phobia will be more likely to apply a patch-like device because of its painlessness, promoting self-administration.

tissue necrosis factor (TNF), and C-reactive protein (CRP), in the wound fluid indicate a stalled or worsening condition and even dehiscence (opening of the affected area).

Many of these biomarkers are commonly found in the biosensor literature, and have been shown to be detectable with standard electrochemical methods. For treatment of these cases, there are several types of drugs that are meant to be directly released to the wound including antimicrobial or antibiotics (such as gentamycin, ofloxacin, minocycline, tetracycline, etc.) that combat infections and growth factors (transforming growth factor-b1 [TGF-b1], platelet derived growth factor [PDGF], human growth hormone, endothelial growth factor, fibroblast growth factor [FGF], etc.) that promote cell production. In one implementation, the tracking of both skin temperature and the concentration level of CRP can be combined. CRP is a commonly detected protein, near a wound site, and its detection can be used to deliver growth factors to the affected area.

Figure 4A:
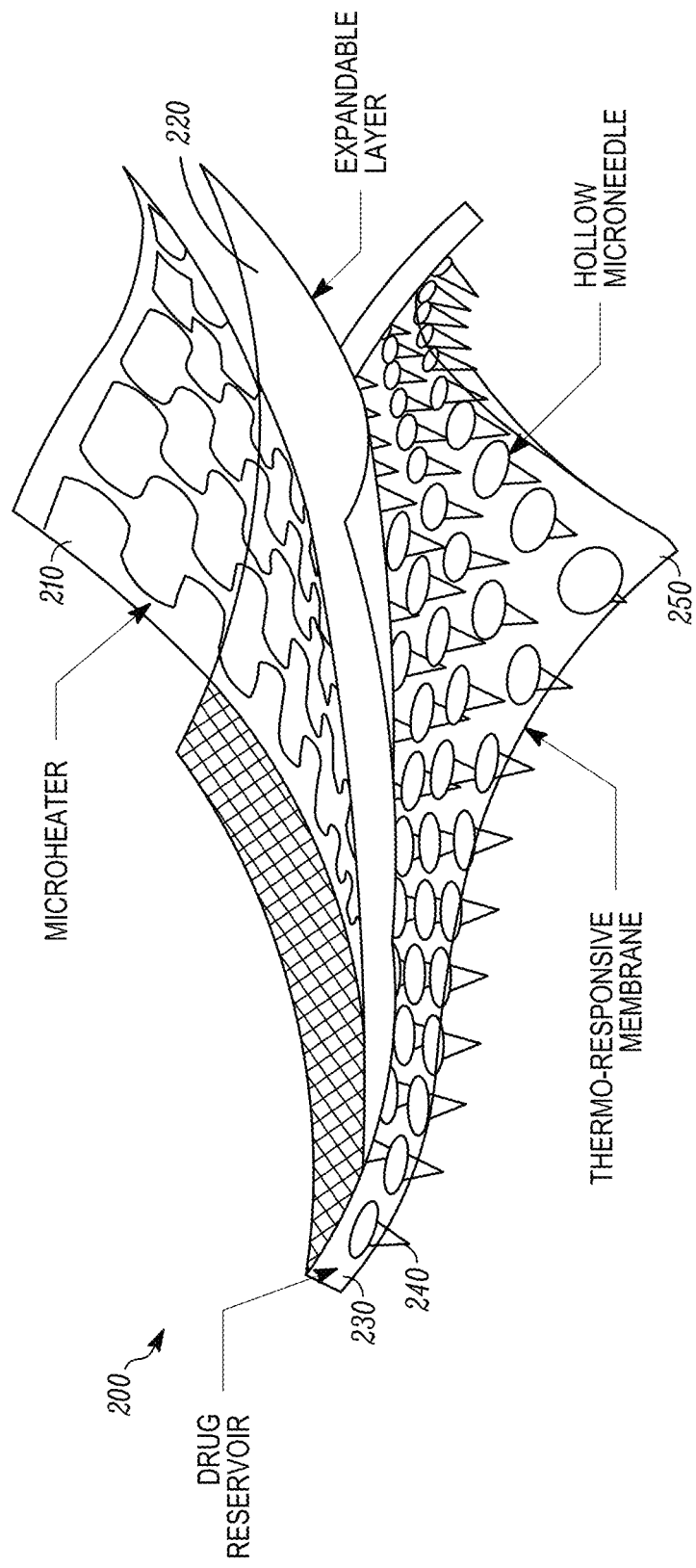
FIGS. 4a and 4b show an example of an actuator array that is formed as a hollow microneedle array.
Figure 4B:
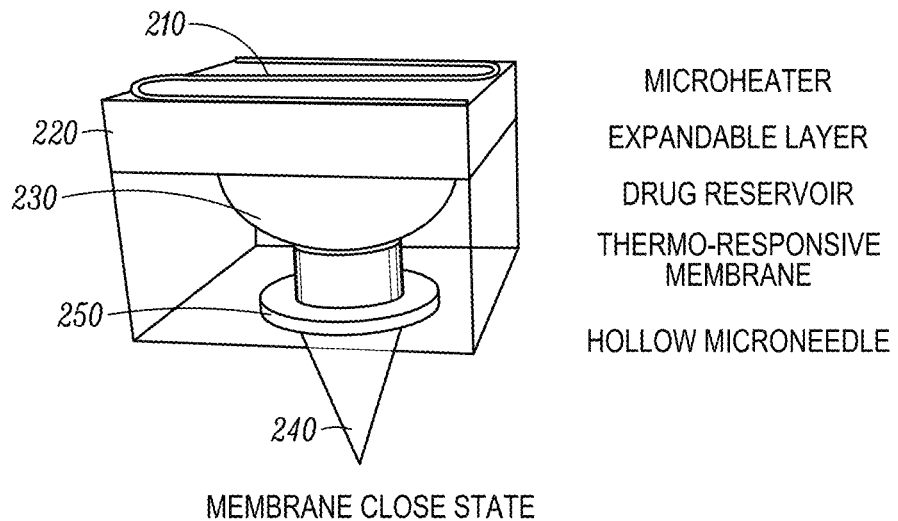

As previously mentioned, the particular example of an actuator shown in FIG. 1 is a hollow microneedle array. One example of such an array is shown in FIGS. 4a and 4b. The microneedle array 200 includes three primary layers: a micro-heater layer 210, an expandable layer 220, and drug reservoir layer 230 through which the individual hollow microneedles 240 extend. A thermo-responsive membrane layer 250 surrounds each microneedle 240 to control the flow of the drug into the microneedle.

TABLE 1

| Type | Advantages | Disadvantages |
| --- | --- | --- |
| Iontophoresis | Non-invasive<br>Local or systemic drug administration<br>Faster than the usual typical routes<br>Allows high concentrations in the target tissue, with limited toxicity | Sensation of tingling or itching, burns<br>Skin irritation (Erythema, oedema)<br>Costly<br>Complex skin pharmacokinetics and difficult to predict |
| Electroporation | Enhanced skin permeability with differing lipophilicity and size.<br>Improved therapeutic efficacy | Low cell viability (typically, 20-50%) due to excessive electrical energy<br>Low transfection rate<br>A sensitive and complicated process |
| Skin Ablation | Local drug administration<br>1000-fold increase of permeability of after heating the skin to 300° C. | Significant temperature rises<br>Deeper tissue removal<br>Limited exposure time (~μs)<br>Require bulky and costly devices |
| Microneedles | Materials and structure versatility<br>Precise delivery on a wide range of localizations<br>Dramatically increased number of drugs that can be delivered<br>Painless, no needle-phobia, no-bleeding<br>No need for expert training<br>Low cost | Drugs and biopharmaceuticals should be protected during incorporation into microneedles and during subsequent storage<br>Mild, transient skin irritation (mild erythema → based on microneedle's length) |

Figure 5:
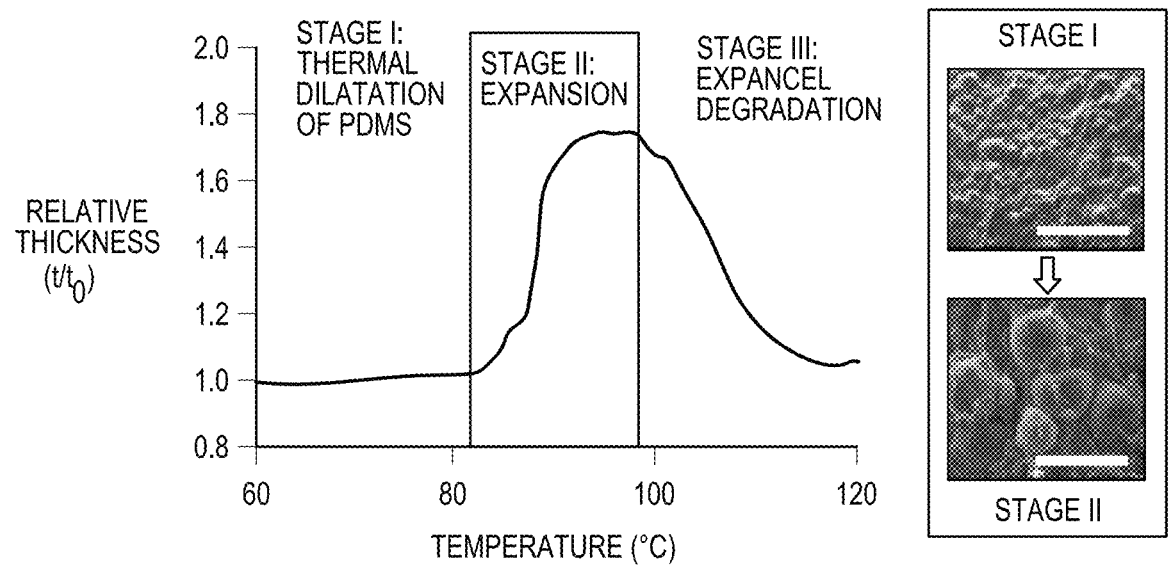
FIG. 5 shows the variation in the thickness that occurs with changes in temperature for one example of an expandable material that may be employed in the actuator array of FIGS. 4a and 4b.

While the wearable platform described herein may be used in a wide variety of skin sensing and drug actuation applications, one particular application concerns wound monitoring and healing. The actual process of healing, consisting of several complex overlapping states, begins with the inflammation state, which is characterized by a rise in temperature due to the rush of blood to the affected area. Hence, by monitoring localized temperature over time, the state of a wound can be tracked to determine if the rate of healing is within normal bounds or if infection or other complications have occurred. Furthermore, in wounds that become chronic, a rise in skin temperature (>4° F. in the case of diabetic ulceration) can be used as an early predictor of reoccurrence before any changes in a wound's physical appearance occur. On the biomolecular side, the presence and increase in concentration of several inflammatory biomarkers, such as interleukin 6 (IL-6), interleukin 8 (IL-8), In operation, controlled release of the drug from the drug reservoir 230 occurs when the control system applies a low voltage (e.g., 1 V) to the micro-heaters in the micro-heater layer 210 located over the expandable layer 220 and the drug reservoir layer 230. The generated heat from the micro-heaters raises the temperature of the expandable layer 220 and at some elevated temperature (e.g., 80° C.) causes the expandable layer 220 to swell, thereby exerting pressure on the drug-reservoir layer and squeezing the drug out from the reservoir layer 230. The expandable layer 220 may be formed, in one embodiment, from an expanded polymer that may include a mixture of PDMS and microspheres. The variation in the thickness that occurs with changes in temperature is illustrated in FIG. 5 for one such material of this type. FIG. 5 also shows SEM images of the expandable microspheres after expansion (scale: the illustrated bars are 100 μm).

At the same time, the heat generated by the micro-heaters also control thermos-responsive membrane layer 250, causing its pores to open. As a result, the drug flows out through the hollow microneedles 240 into the epidermal skin. This transformation of the thermos-responsive membrane is reversible upon cooling when the drug release needs to be halted.

The hollow microneedle array 200 may be fabricated in a number of different ways. For instance, in embodiment it may be realized in two steps. In the first step a silicon mold is constructed that defines profile of the pyramidal tip. The process begins with a (100) silicon wafer, coated with a $Si_3N_4$ film deposited by plasma-enhanced chemical vapor deposition (PECVD). The $Si_3N_4$ is selectively removed by conventional photolithography and reactive ion etching (RIE) followed by an anisotropic KOH wet etching, which defines the pyramidal pits in Si (100) substrate.

In the second step of the fabrication process forms the hollow microneedle on the intermediate silicon mold that has been constructed. Prior to SU-8 coating, chromium black is deposited on the silicon mold to reduce undesired back scattering, which may result in the occlusion of the lumen in the individual microneedle. Then, SU-8 is coated on the silicon mold and cross-linked by lithography. In this step, the shaft and lumen in individual microneedle are formed. A second exposure is performed to define the baseplate that locates on the top of SU-8. After a post exposure baking and following developing, the completed hollow microneedle array is peeled off from the silicon mold.

The micro-heater layer 220 is formed by coating the silicon substrate with PMMA, followed by spin casting of polyimide (PI) for encapsulation of the microheater. A thin layer of Cr/Au is deposited onto the PI, and microheater patterns are defined by sequential lithography steps and wet etching.

The expandable layer 220 may be fabricated with a mixture of PDMS and expandable microspheres in a 2:1 ratio and spin coated onto the PI with the microheater. Then, hemispherical shaped reservoirs made of e.g., cyclic olefin polymer (COP), are affixed to the expandable layer 220 using double-sided adhesive tape. The PMMA is then removed by immersing it in acetone. Prior to liquid phase drug loading, the inside of reservoir may be treated with oxygen plasma to make inner surface hydrophilic. Then, to prevent evaporation and diffusion-based leakage of the drug, the outlets of reservoir are hermetically sealed with a thermos-responsive membrane. Liquid drug drops can be dispensed into the cavities using a syringe to load the drug. The hollow microneedle array 200 may be completed by assembling the microheater layer 210, expandable layer 220, and the drug reservoir layer 230 with the hollow microneedles 240. Alignment and bonding between each layer can be achieved with a UV ozone treatment.

Although the hollow microneedles punctures the stratum corneum, which usually acts as a barrier for ingress of microorganisms, there have been no reports of this technology causing skin or systemic infection. The application of such devices to the skin is painless and causes no bleeding; the short length of these microneedles reduces the likelihood of encountering and/or stimulating a dermal nerve and/or reaching a dermal blood vessel. Recently, there was a report arguing that microneedle puncture results in significantly less microbial penetration than hypodermic needle puncture and that no microorganisms crossed the viable epidermis in microneedle punctured skin, in contrast to hypodermic needle-punctured skin. Given the antimicrobial properties of skin, it is likely that application of microneedle arrays to skin in an appropriate manner would not cause either local or systemic infection in normal circumstances in immune-competent patients. Additionally, safety in patients will be enhanced by aseptic or sterile manufacturing.

In one embodiment, the drug reservoir itself may be formed from cyclic olefin polymer (COP) because it has high moisture barrier properties (water permeability: 0.02-1.0 g·m$^2$/day) compared with that of conventional polymers. The permeability of COP can be further lowered by the application of parylene, which has also a low water permeability. This promotes stability of reagent concentrations (i.e., drugs) and provides longer device shelf life of moisture-sensitive compounds. There are several other choices pertaining to the physical and chemical properties of COP that make it an excellent material for the drug reservoir. First, it has low outgassing characteristics. Compared with conventional barrier polymers for drug packaging such as polycarbonate and polypropylene, COP has significantly reduced risk of contamination from outgassing extractables. Second, COP shows significantly lower protein adsorption rate compared with polypropylene and glass. This is an optimal condition for loading protein-based drugs. Third, COP has exceptional chemical resistivity to those that are commonly used in the pharmaceutical industry.

As an alternative to the hollow microneedle array 200 described above, another type of drug delivery device that may be employed is a porous membrane that can contain the drug(s) or other agents and control their release rate. While any of a wide variety of such porous membranes may be employed which can control the diffusion rate of the drug or agent, one particular example that may be employed is a silicone elastomer such as the aforementioned material known under the tradename Ecoflex®. By saturating the pores of this material with the desired drug or agent, the drug or agent can be releasably controlled by the application of a current.

Figure 6:
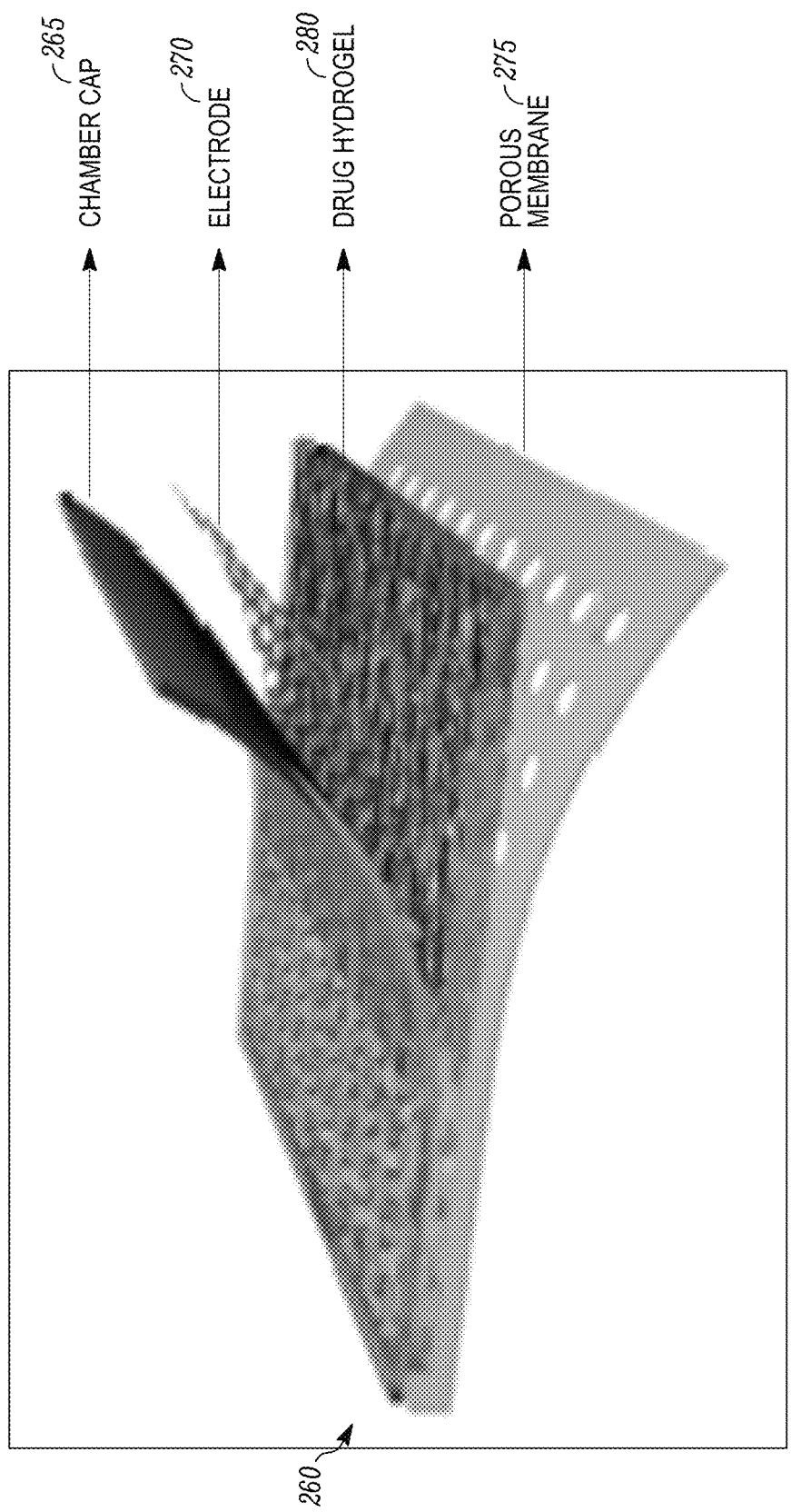
FIG. 6 shows one example of a drug delivery device that employs a porous membrane.

FIG. 6 shows one example of a drug delivery device that employs a porous membrane. In this example the drug delivery device constitutes a pouch or chamber 260 that includes three primary layers: a chamber cap 265 that may be formed from an elastomer material, an electrode layer 270 and the porous membrane 275. As further indicated in FIG. 6, the porous membrane 275 is saturated with a fluid 280 that includes a mixture of a drug or other active agent and a hydrogel in order to increase the viscosity of the fluid.

Figure 7:
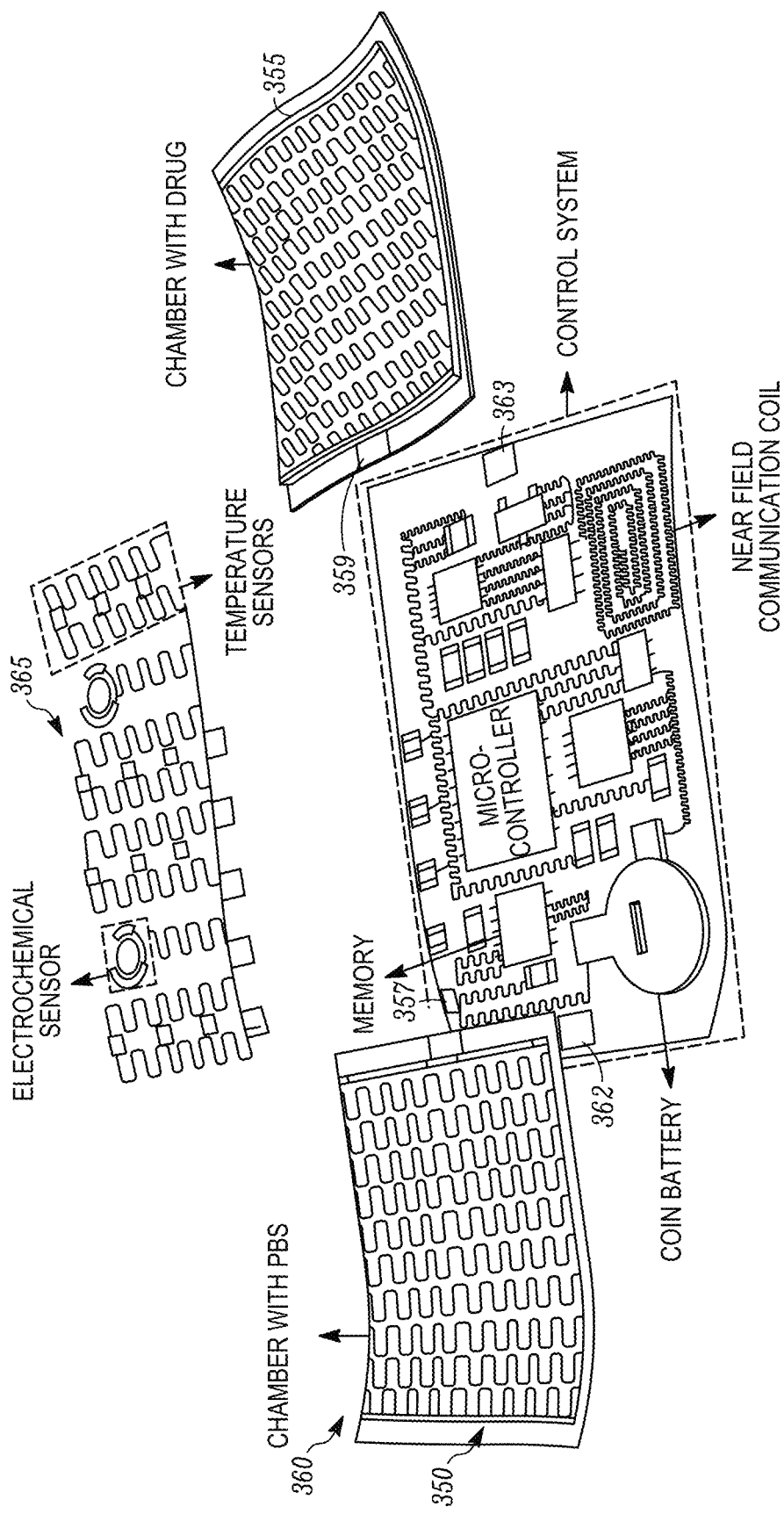
FIG. 7 shows an expanded view of another example of a closed-loop wearable platform or device that includes two drug delivery chambers of the type shown in FIG. 6.

FIG. 7 shows an expanded view of another example of a closed-loop wearable platform or device 360 that includes two drug delivery chambers 350 and 355 of the type shown in FIG. 6. In this example drug delivery chamber 350 is used to deliver PBS (phosphor buffered solution) while drug deliver chamber 355 can be used to deliver a different drug. The chambers 350 and 355 serve as modules that can be directly applied to the underlying elastomer substrate (which may be the substrate that includes the control system 360) and held in place by van der Waals forces. In this way the chambers 350 and 355 can be removed and replaced when necessary. The chambers 350 and 355 include electrically conductive bonding pads 357 and 359, which establish an electrical connection to corresponding bonding pads on the underlying substrate, such as pads 362 and 363 shown on the control system module 360. Also shown in FIG. 7 is a sensor module 365 that includes an electrochemical sensor array and a temperature sensor array. The sensor module 365 may also be removably attached to the underlying substrate in a manner similar to the drug deliver chambers 350 and 355.

In some embodiments the drug delivery chamber may be used to deliver a drug in accordance with iontophoresis. In an iontophoresis process, a charged substance such as a drug or other agent is driven by a repulsive electromotive force through the skin. A small electric current is applied to the chamber that contains the charged drug and its solvent when the wearable device is placed on the skin. Another electrode carries the return current. The positively charged electrode repels the positively charged chemical species and the negatively charged electrode repels a negatively charged species, driving it into the skin.

Figure 8:
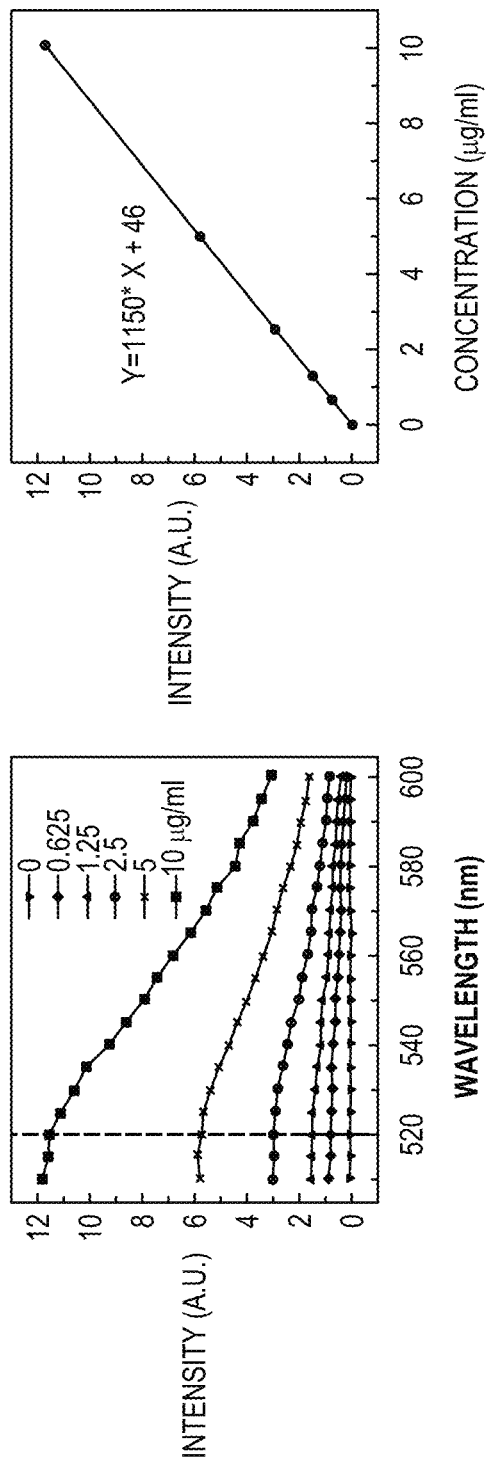
FIG. 8(a) shows the fluorescence spectra of a drug (curcumin in this example) with different concentrations that is delivered by iontophoresis.
FIG. 8(b) is a calibration curve showing the linear relationship between the fluorescence intensity and drug concentration.
FIG. 8(c) shows the drug delivery speed when no current is applied (corresponding to a passive state), when a reverse current is applied to hold the drug in the chamber (corresponding to a control state), and when a forward current is applied to the chamber (corresponding to an active state) to drive the drug into the skin.
Figure 8:
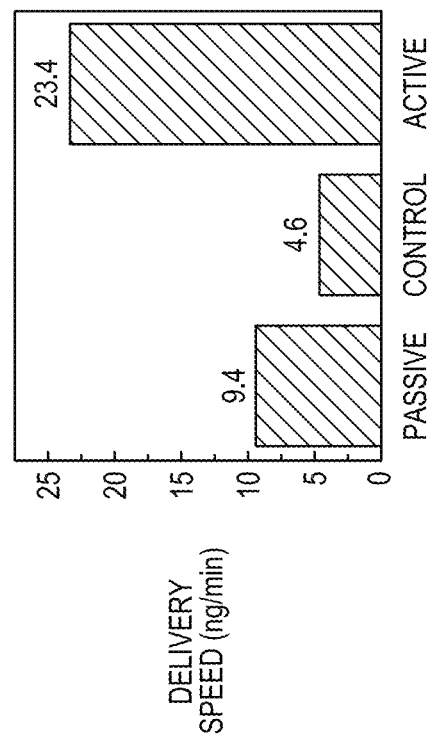

FIG. 8(a) shows the fluorescence spectra of a drug (curcumin in this example) with different concentrations that is delivered by iontophoresis FIG. 8(b) is a calibration curve showing the linear relationship between the fluorescence intensity and drug concentration. FIG. 8(c) shows the drug delivery speed when no current is applied (corresponding to a passive state), when a reverse current is applied to hold the drug in the chamber (corresponding to a control state), and when a forward current is applied to the chamber (corresponding to an active state) to drive the drug into the skin.

Electrochemical Biomarker and Temperature Sensor Module

Figure 9:
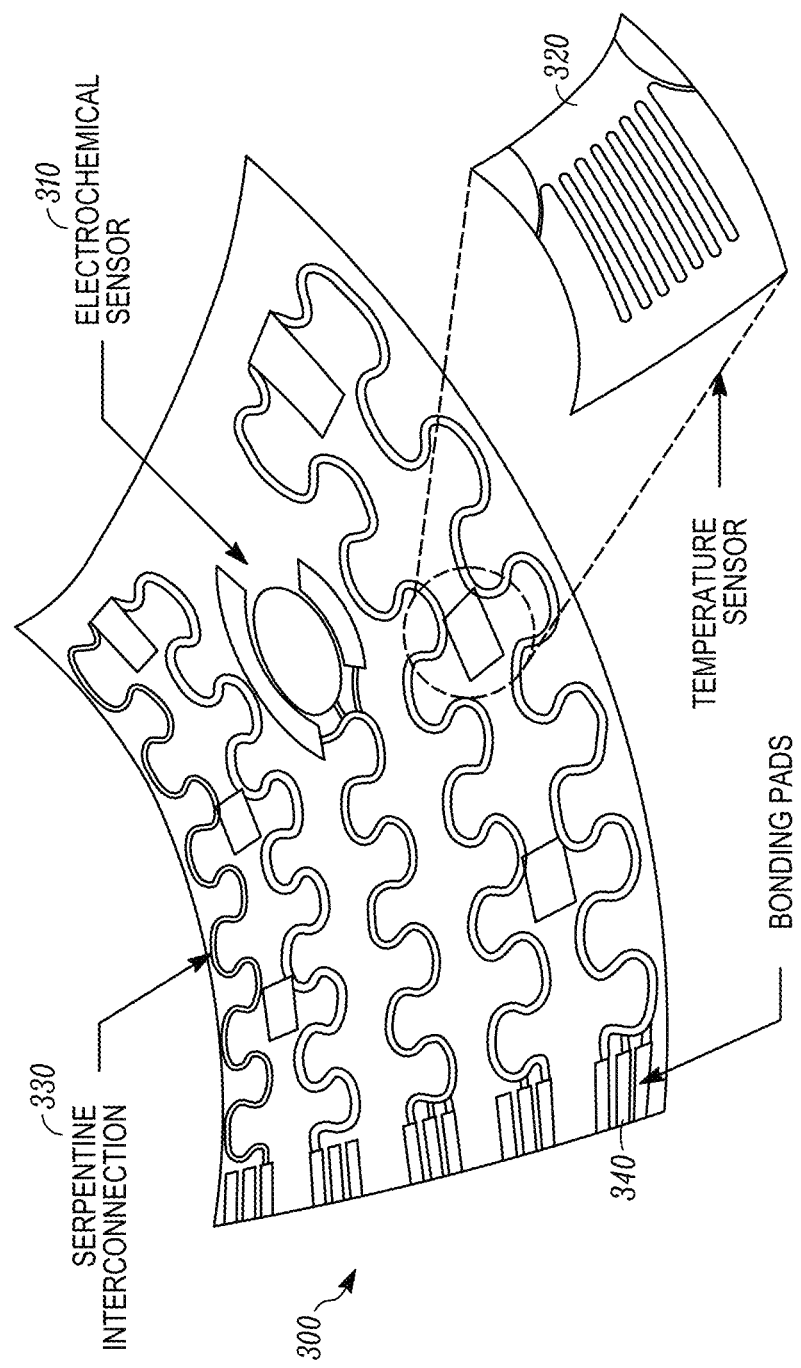
FIG. 9 illustrates one example of a sensor module which incorporates a temperature sensor array and an electrochemical biomarker sensor array.

FIG. 9 illustrates one example of a sensor module 300 which incorporates a temperature sensor array and an electrochemical biomarker sensor array. The sensor module 300, which may be incorporated in the closed-loop wearable device shown in FIG. 1, includes electrochemical biomarker sensors 310 and temperature sensors 320, which are interconnected by serpentine electrical interconnects 330. Electrically conductive bonding pads 340 are provided for establishing an electrical connection between the sensor module and the other modules and components on the wearable platform. The electrochemical sensors, which may be controlled by potentiostat circuitry that applies the necessary electrical signals to activate the sensors and measure the resulting signal, are functionalized with a detection bioelement used to achieve high specificity while using a label-free sensing technique. An array of temperature dependent metal film resistors, integrated next to the biosensor, can interrogated by the same microcontroller that controls the electrochemical detection. There are several challenges that arise from integrating and optimizing each of these components for wearable devices that are used to detect sweat from the skin, such as the significantly lower concentration of protein biomarkers on the surface of the skin than in other bodily fluids, the need for small non-rigid reusable circuitry, and the desire to make the entire measurement process automatic without interference from the user. The following sections describe how these issues can be addressed.

Since space is a highly constrained resource on a wearable platform, and because the electronics need to be integrated with a flexible substrate that lacks routing layers and vias, more traces and connections come at the cost of increased layout and routing complexity. Hence, the potentiostat that is employed to control the transducers, which may be made entirely from commercial off-the-shelf (COTS) parts, should have a design that minimizes the number of components and which have as few pins as possible. In addition, if the system only requires the use of EIS, the potentiostat can be slimmed down to simply function as a dedicated impedance detector.

The potentiostat may include an analog front end that interfaces with the transducers. In one embodiment the transducers are electrodes made from chemically inert metals. Due to the small size and spacing of the sensor and to introduce minimal voltage error, a two-electrode system can be used, consisting of a working electrode (e.g., a gold electrode) and the reference electrode (e.g., a silver/silver-chloride electrode), as it reduces the number of traces required for the electronics and sensor surface. The electrodes (at least two sets in order to have control) can be printed directly onto the flexible substrate and manually functionalized by pipetting the bioelement directly onto the gold surface.

Electrochemical Biosensors

In some embodiments, the wearable platform described herein may employ any combination of one or more types of electrochemical biosensors. The detection of different analyte types such as ions, metabolites, proteins, and amino acids each requires a different electrochemical method in order to measure and quantify them in sweat. Typically, potentiostatic methods coupled with ion selective electrodes (ISE) are used to detect ions (sodium, potassium, calcium, etc.), while amperometric techniques are used to induce reactions and sense certain metabolites such as glucose and lactate through enzymatic reactions. However, for proteins, sandwich assays with electrochemical enzyme tags, which bind to the desired analyte, are commonly used to detect these larger molecules. This method can achieve both high selectivity due to the specificity of the ligand-analyte binding and high sensitivity from the enzyme catalyzed amplification of the electrochemical signal. However, these assays, which take advantage of a label or tag, require additional mixing, incubation, and washing steps that significantly complicate lab-on-a-chip type devices. In some embodiments point-of-care oriented electrochemical biosensors that have been previously developed may be employed which are able to interface with mobile devices such as smart phones and which can run a wide variety of electrochemical assays. Example of such biosensors as described in A low-cost smartphone-based electrochemical biosensor for point-of-care diagnostics, A. Sun et al., *Biomedical Circuits and Systems Conference* (BioCAS), 2014 IEEE, which is hereby incorporated by reference in its entirety.

In one embodiment, to reduce the regents used, shorten the measurement time, and avoid these difficult extra steps, a highly sensitive label-free technique can be used known as electrochemical impedance spectroscopy (EIS). With EIS, the impedance between electrodes functionalized with detection biomolecules, such as antibodies, diabodies, synbodies, aptamers, and single-stranded nucleic acids are measured and an increase in surface impedance represents that the analyte has been bound to the surface. This technique is especially sensitive when measuring changes that occur at the surface of these electrodes, which are typically made of inert metals such as gold, platinum, or silver. Capture ligands are attached to these surfaces and a solution possibly containing antigens is introduced to the cell. Any antigen-antibody binding that occurs will impede charge-carrying molecules from reaching the electrode and displace ions that have gathered near the surface causing a measurable impedance shift.

EIS works by applying multiple small sinusoidal voltage signals (e.g., voltages less than 10 mV amplitude) at varying frequencies from e.g., 0.1 Hz to 100 kHz, between electrodes in an ionic solution and measuring the current signals that result. The amplitude and phase data is then fitted to an equivalent circuit model called a Randles circuit, which models the electrical interface between the electrodes. It is then used to obtain resistance changes that correlate to the binding of biomarkers to the surface of the electrodes. Detection can be quantified by tracking the double layer capacitance ($C_{dl}$) created by the formation of ions and charged molecules near the electrode surface. Hence, physical displacement of these charges produces a change in the dielectric properties of the electrode-solution interface thereby altering the double layer capacitance. Binding can also be measured by extracting the resistance ($R_{ct}$) created by the redox molecules reacting and transferring electrons, also known as the charge transfer resistance.

Figure 10:
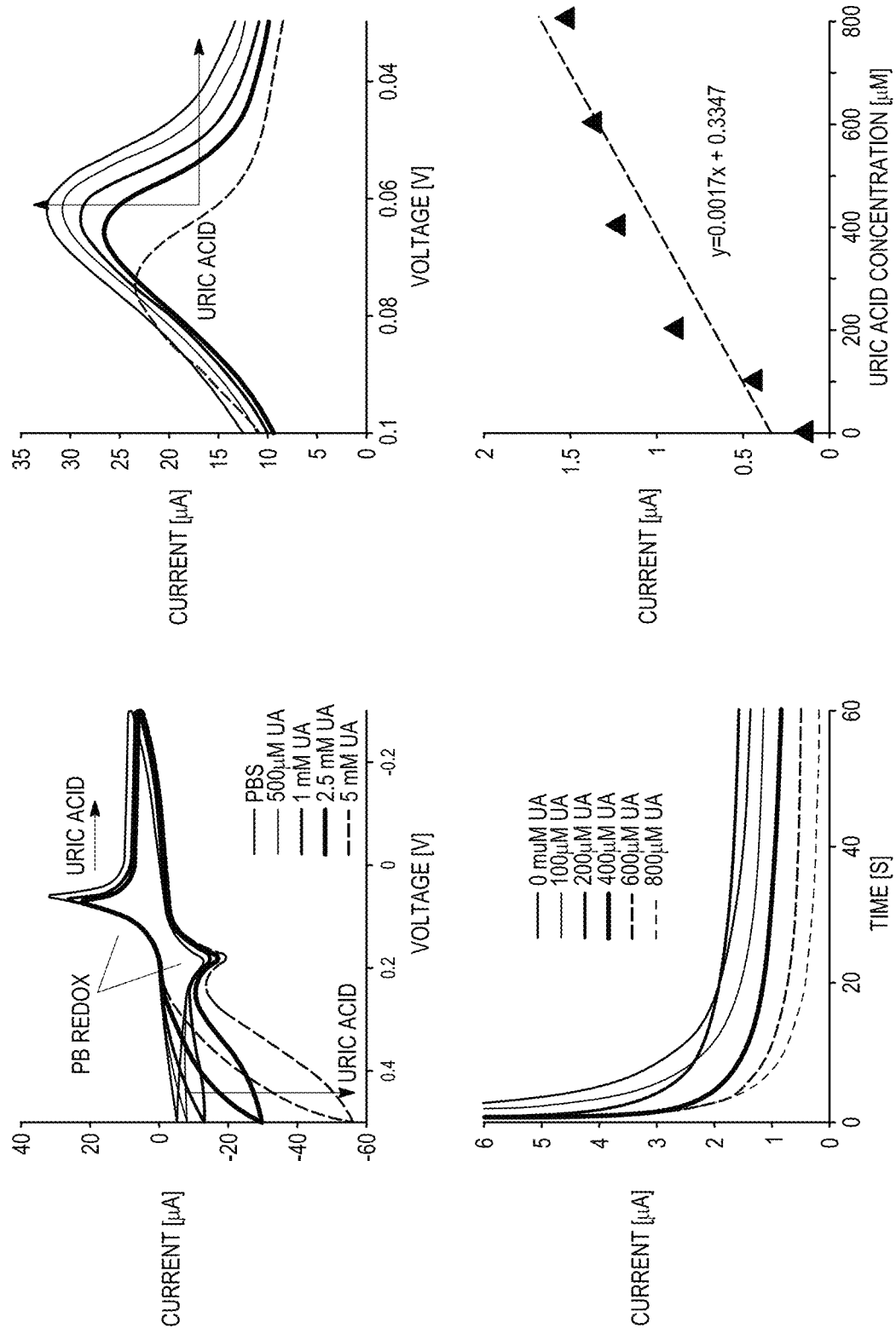
FIGS. 10(a)-10(d) show illustrative measurements obtained from an electrochemical sensor that is used to detect uric acid.

FIGS. 10(a)-10(d) show illustrative measurements obtained from an electrochemical sensor that is used to detect uric acid. FIG. 10(a) shows cyclic voltammetry of uric acid reaction with uricase. FIG. 10(b) shows $H_2O_2$ detection in the presence of a PB mediator. FIG. 10(c) shows chronoamperometry of uric acid at −0.1 V and FIG. 10(d) is a calibration curve that shows the sensor sensitivity to be approximately 1.7 nA/μM.

Temperature Sensor

As previously mentioned, in some embodiments the closed loop wearable platform may include a temperature sensor array. Such an array may combine multiplexed coefficient of resistance (TCR) sensors with interconnect traces that are arranged, for example, in a filamentary serpentine mesh. The filamentary mesh design minimizes strain in the sensor and the interconnects during deformation, resulting in a small effect of strain on resistance. Top and bottom layers of a polyimide (PI) encapsulating metal can be used to provide electrical insulation and a moisture barrier. This sandwiched configuration also places the metal close to the neutral mechanical plane, for improved mechanical robustness. A distributed array of such temperature sensors can be used to provide a spatial map of temperature over the skin.

Figure 11:
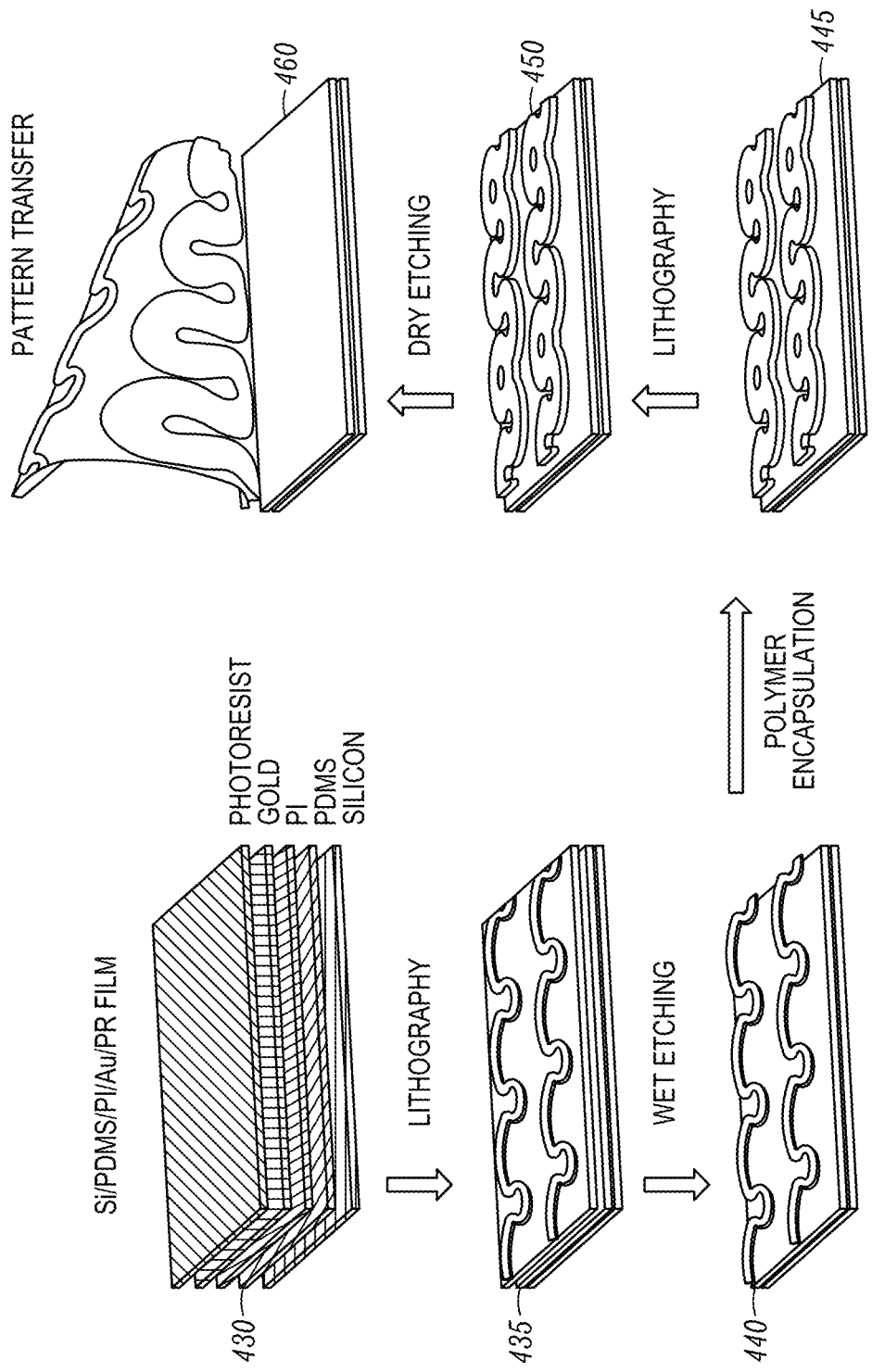
FIG. 11 illustrates one example of the microfabrication steps that may be employed to fabricate one embodiment of a temperature sensor array.

FIG. 11 illustrates one example of the microfabrication steps that may be employed to fabricate the temperature sensor array described above. The process begins with spin casting of polydimethylsiloxane (PDMS) onto a clean Si wafer. After curing in an oven, the PDMS is exposed to oxygen plasma for surface activation, which increases the adhesion to a layer of PI sequentially spin-coated on top. The interconnects and metal electrodes, consisting, in one embodiment, of a layer of Cr/Au, are deposited by electron beam evaporation onto the PI. Photolithography and etching defines patterns in the Cr/Au. Next, spin coating forms a second layer of PI over the entire structure. Photolithography defines the regions where the unmasked PI layer is etched, which results in an encapsulation of the metal electrode and interconnection with the top and bottom layers of PI with a geometry matched to the metal traces. Then, a water-soluble tape (such as available from 3M, for example) retrieves the completed patterns from the carrier wafer for subsequent transfer and covalent bonding onto a silicone membrane (e.g., Ecoflex®), which exhibits a low Young's modulus (e.g., about 60 kPa) that is in the same range as skin epidermis. To provide electrical isolation for clinical use, a material such as a 5-μm-thick layer of silicone is coated on the top of patterns.

The temperature measuring circuit is composed of the TCR sensor array and the multiplexer and current source of the control system. The multiplexer selects one of several analog or digital input signals and forwards the selected input into a single line. Through multiplexing, temperature measurements from the individual sensors in the TCR sensor array are sequentially obtained. In the TCR sensor array, the individual TCR sensors serve as a resistance thermometer, also called as resistance temperature detector (RTD), which is used to measure temperature by correlating the resistance of the RTD element with specified temperature. The resistance is calculated from the measured voltage. The TCR sensors operate using the four-point probe technique. The applied current should be carefully selected to prevent self-heating of individual sensors in the array.

Calibration of the individual TCR sensors may be performed with a hotplate that is able to tune its temperature to within e.g., 1° C. In one example a flat black hot plate with an emissivity of 0.96 may be used. After stabilization of the hotplate temperature, the TCR sensor array is mounted on the hotplate. This calibration arrangement reduces the piezoresistance changes associated with mechanical deformation in the mounting step, thereby providing improved precision in calibration. The calibrations include several temperature six points between 25° C. and 50° C. After allowing system to come to thermal equilibration over a period of time, e.g., 10 minutes, the surface temperature on the black plate near the device may be recorded by an IR camera. At the same time, the voltage and corresponding resistance value of each sensor is recorded for e.g., 20 seconds. This measurement is repeated for a total of several, e.g., six, temperature points from 25° C.-50° C. Based on the recorded value, the linear relationship between resistance and temperature is derived within the test range of temperatures.

Figure 12:
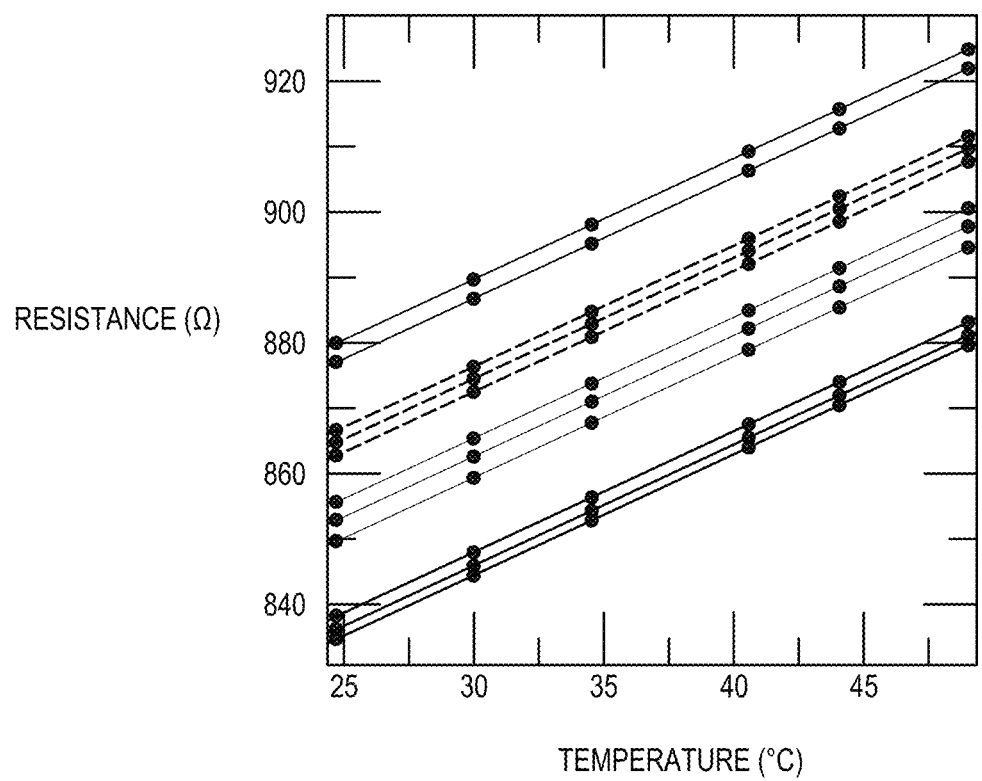
FIG. 12 shows illustrative temperature calibration curves for a number of temperature sensor samples.

FIG. 12 shows temperature calibration curves for a number of sensor samples. The curves are arranged in four groups largely due to the difference in interconnect distances between the sensors in different groups. The linear function that determines the temperature can be obtained by a least squares method, which is used to generate the calibration curves.

The response time of the temperature sensors are closely related to the thermal mass of the soft materials constituting the TCR sensor array. Since the TCR sensor array is composed of materials with extremely low thermal masses per area and high water/gas permeability they provide a fast response time. For the TCR sensors that have a direct contact to the skin without use of an elastic backing layer, the estimated thermal mass per unit area is about 150 μJ·$cm^{-2}$·$K^{-1}$, which is identical to that of human skin with a thickness less than 500 nm. If, for instance, an elastic backing layer with a thickness of approximately 50 μm is employed to support an iterated attachment and removal process, the thermal mass per unit area increases to 7.2 mJ·$cm^{-2}$·$K^{-1}$ (which is equal to a skin thickness of less than 25 μm). In addition, the response time is also affected by thermal inertia, the material property by which a mass tends to maintain its initial temperature. Thermal inertia of the temperature sensor system is approximately 500 W·$s^{1/2}$ $m^{-2}K^{-1}$, smaller than the thermal inertia of skin, which is 1000~2000 W$s^{1/2}$ $m^{-2}K^{-1}$. Due to the low thermal mass and inertia, the temperature sensor array can provide a fast response of 10~100 ms.

In some embodiments a temperature sensor as described in, *Ultrathin Conformal Devices For Precise And Continuous Thermal Characterization Of Human Skin*, R. Chad et al., Nature Materials 12, 938-944 (2013), which is hereby incorporated by reference in its entirety.

Control System

The control system 120 shown in FIG. 1 employs a preprogrammed microcontroller to distinguish between normal and abnormal levels of various vital signs. The actuators will not be active until an abnormal electrophysiological signal is detected or the user instructs them to do so. For instance, if the drug delivery device employs a microneedle array such as shown in FIG. 4, the microcontroller will turn on the micro-heater array that swells the soft elastomer layer when abnormal signals are detected. Therefore, the stored drug or other agent is squeezed out of the reservoirs and injected into the epidermal layer of the human skin through the hollow microneedle arrays.

Figure 13:
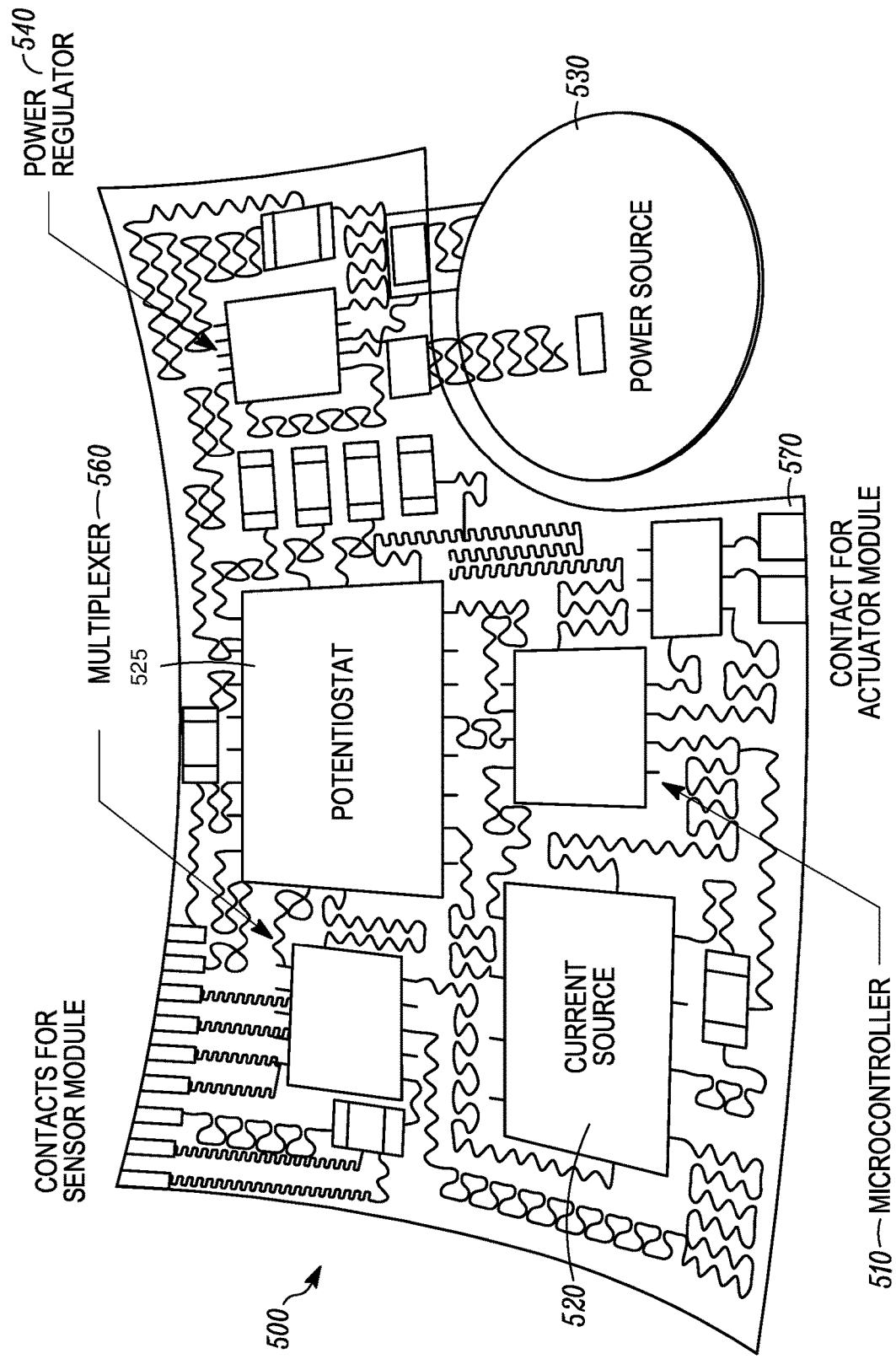
FIG. 13 illustrates a more detailed example of the control system shown in FIG. 1.
Figure 14:
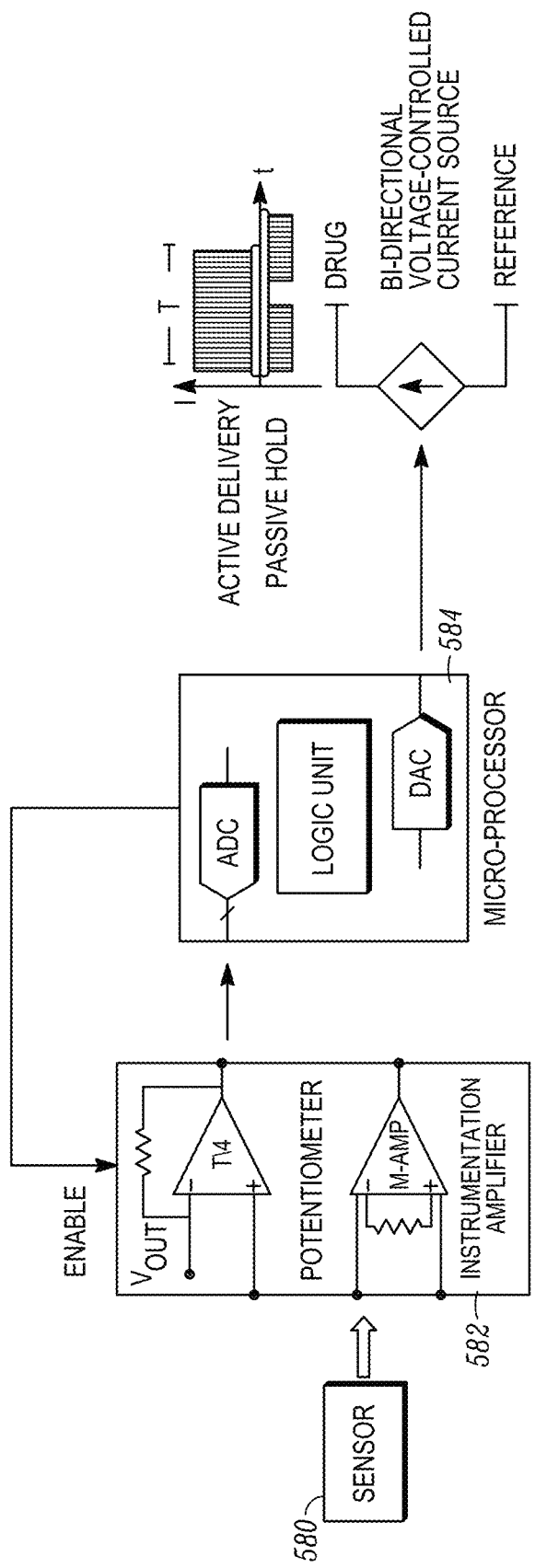
FIG. 14 shows a high level functional block diagram of the overall control process performed by the control system of FIG. 13.

FIG. 13 illustrates a more detailed example of the control system shown in FIG. 1. The control system 500 includes a microcontroller 510, a potentiostat 525, a current source 520, a power source 530, a power regulator 540, a multiplexer 560 and contacts 570 for communicating with the sensor module and the actuator module. FIG. 14 shows a high level functional block diagram of the overall control process which includes sensors 580, sensor readout circuitry 582 that receives signals from the sensors 580, which in turn are provided to a microprocessor 584. Microprocessor 584 will analyze the sensors data, make a decision and 586 for drug delivery or drug hold. The rightmost portion of the figure shows the current source 586 signal when the drug delivery chamber is to be in its active state delivering a drug or other agent and when it is to be in its passive state to prevent or minimize drug delivery.

In one embodiment, all the electronic components, except the serpentine metal connectors and micro-heater electrodes, including the microcontroller, passive components, multiplexers, etc., can be commercial, off-the-shelf, surface-mount chips. The chips can be mounted on the membrane substrate and electrically connected to the serpentine interconnects using hard/soft integration techniques. Commercial off-the-shelf (COTS) chips offer integrated functionality and are critical building blocks for conventional electronics, but their mechanical incompatibility with the soft elastic device structures make their direct incorporation difficult. To manufacture a stretchable/flexible electronic system, both the passive and active components must be seamlessly integrated into one soft package.

A key challenge for incorporating COTS components into soft systems is to integrate the hard discrete components (~8 mm×8 mm×3 mm in L×W×H; 10 GPa modulus; up to 1% failure strain) with compliant elastomeric substrates (~30 mm×30 mm×0.1 mm in L×W×H; 0.1-1 MPa modulus; up to 900% failure strain) without building up at the hard/soft interface a large amount of strain, which would cause chip delamination and device failure. The larger the COTS chip, the higher the interfacial strain.

When under deformation, strain can build up at the hard chip-soft substrate interface, leading to delamination and device failure. Patterned surface chemistries of the elastomeric substrate may be engineered to selectively bond a small area of the device components, achieving effective mechanical isolation. The resulting device can achieve an elastic modulus only slightly higher (e.g., 3%-5%) than that of the soft substrate itself, making the integration essentially "mechanically invisible".

To further reduce strain between the hard chip and soft substrate, the control system may be packaged using a liquid material or an ultra-low Young's modulus solid packaging material. If such materials are used the components of the control system may be encapsulated within a containment chamber formed by a substrate and a superstrate. If a low modulus solid is employed, the electronic components can be placed near the neutral mechanical plane and may be supported by both the substrate and the low modulus solid. In some embodiments the thickness of the low modulus solid may be less than about 1000 μm. Moreover, in some embodiments more than one packaging material may be employed within the containment chamber, with each having a different Young's modulus. The two or more packaging materials may be mixed or layered within the containment chamber.

If a fluid packaging material is employed, selection criteria for the fluid may include (1) wettability toward the electronic components and the substrate/superstrate, to facilitate the filling process, (2) large volume resistivity ($>1\times10^{14}$ Ohm*cm) to eliminate electrical crosstalk, (3) high dielectric strength (>10 kV/mm) to avoid electrical breakdown, (4) moderate viscosity (e.g., about 5 Pa·s) to enhance impact resistance, (5) good thermal stability (e.g., weight loss less than 0.1% at 100° C. for 4 hours to allow reliable long-term operation, (6) low loss RF properties and small dielectric constant (e.g. less than 3), to minimize influence on RF operation, (7) low reactivity and chemical stability, to avoid corrosion or other forms of chemical degradation, (8) hydrophobic character, to expel moisture from the package and (9) optical transparency to enable rapid inspection of the components. Although many materials can be considered, in some embodiments a soft, silicone elastomer such as the aforementioned Ecoflex may be used for the substrate/superstrate, and a high molecular weight silicone oligomer (e.g., Sylgard 184, without curing agent) may be used for the fluid.

To reduce the thickness of the functional COTS chips, they can be mechanically polished by removing the encapsulating epoxy materials, leaving behind the bare dies plus the wire bonding loops. In this way, the overall chip thickness can be reduced down to from about 2 mm to 1 mm. To further decrease the device thickness, bare dies without wire bonding connections, which are an order of magnitude thinner than their COTS chip counterparts, may be employed. This approach allows the reliable incorporation of integrated circuits—which are the basis of modern electronics—with soft systems without sacrificing the mechanical stretchability.

By combining strategies in materials, microfluidic systems, structural designs and mechanics theory for low modulus, stretchable systems that incorporate assemblies of high modulus, rigid, state-of-the-art functional bare die elements, a thin, conformable device that can softly laminate onto the surface of the skin can be produced, which allows advanced, multifunctional operation for physiological monitoring. The capability to integrate rigid materials into a flexible or stretchable lattice bridges the gap between hard and soft. The versatility of these approach its compatibility with other approaches to flexible/stretchable electronics suggest a foundation for rapid progress in wearable devices that exploit intimate integration with the human body.

Serpentine Interconnects

The wearable devices described herein exploit island-bridge architectures, in which the active components reside at the islands and the electrical interconnects form the bridges; the latter are largely responsible for the stretchability. Generally, they must accommodate two competing design goals: (1) high areal capacity, which requires large coverage of the active regions, and (2) high mechanical stretchability, which requires large distances between these regions. Strategic features of relief on the elastomer substrates provide a partial solution to this challenge. A disadvantage is that levels of stretchability beyond 30% can be difficult to achieve without sacrificing coverage.

With more advanced structural designs, denser packing may be achieved without sacrificing stretchability. At least two classes of bridge structures have been proposed: (i) straight ribbons in arc-shaped layouts that result from Euler buckling and (ii) serpentine traces that also involve noncoplanar geometries, in either or both the as-fabricated and as deformed states. The first involves a comparatively simple geometry, with deformation mechanisms that have been thoroughly investigated extensively via experiments and fundamental mechanics theory. The serpentine interconnect represents an advanced embodiment, with improved stretchability for a given spacing between adjacent islands. When fabricated in an ultra-thin form and mounted on a thin elastomeric substrate (e.g., polydimethylsiloxane and Ecoflex), the serpentine interconnect could be conformably mounted on the human skin, because of its ultra-soft feature.

Figure 15:
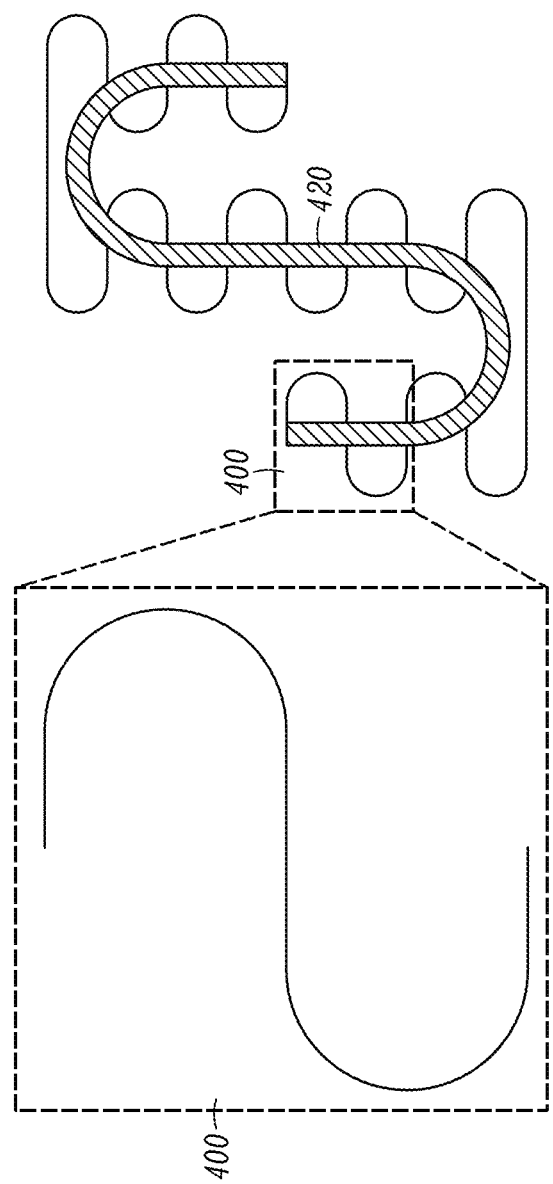
FIG. 15 shows one example of a self-similar serpentine electrical interconnect.

As previously mentioned, in some embodiments the electrical interconnects employed in the wearable devices described herein may have interconnection layouts that use 'self-similar' structures of wires in serpentine configurations to offer, simultaneously, high system level stretchability, and low interconnect resistances. A conventional serpentine consists of circular arcs connected by straight lines. 'Self-similar' designs follow from iteratively applying this basic geometry, beginning with a unit cell 400 as illustrated schematically in FIG. 15. The self-similar serpentine interconnect can then be formed by reducing the scale of the cell and then connecting multiple copies of it in a fashion that reproduces the layout of the original cell geometry. In some embodiments a $2^{nd}$ order serpentine geometry may also be employed, as illustrated by the interconnect 420 in FIG. 15. Although the wearable device may even incorporate higher orders, a $2^{nd}$ order construct is likely to satisfy the requirements for the applications considered herein.

With a hierarchical serpentine design, the impedance between the electrode and skin can be minimized, as well as the signal to noise ratio. In addition, metal wires can achieve a reversible stretchability of 300%. In some embodiments the serpentine interconnects are not bonded to the elastomeric substrate so that they can deform freely and allow the interconnect-substrate interaction to be neglected. Such a serpentine interconnect could be realized in fabrication through two approaches: (i) providing a molded relief structure on the elastomeric substrate, and bonding the islands onto the top of the raised relief; (ii) using a substrate, and selectively bonding the islands onto the substrate, while leaving the serpentine interconnect with only a weak interaction with the substrate.

In some embodiments the interconnects may be fabricated using the techniques described in the aforementioned reference Xu S. et al., *Stretchable Batteries With Self-Similar Serpentine Interconnects And Integrated Wireless Recharging Systems*, Nature Communications, 4:1543 doi: 10.1038/ncomms2553 (2013).

In one particular embodiment, the fabrication process begins by spin casting polydimethylsiloxane (PDMS, Sylgard 184) onto a clean glass slide. After curing in an oven, the PDMS is exposed to oxygen plasma. A layer of polyimide (PI) amic acid solution is then applied by spin casting, baked on a hotplate and in a vacuum oven. The interconnects and metal electrodes consists of a layer of Cu deposited by electron beam evaporation onto the PI. Photolithography and etching defines patterns in the Cu. Next, spin coating forms a second 2.4 µm thick layer of PI over the entire structure. A layer of $SiO_2$ is then deposited using electron beam evaporation, to serve as an etching mask for the PI. Next, photolithography, RIE etching, and oxygen plasma etching patterns the layers of PI in a geometry matched to the metal traces. The residue $SiO_2$ mask is removed using buffered oxide etchant, and the overall circuit electrodes are immersed in electroless Sn plating solution. The Sn deposits only onto the exposed Cu surfaces, for the purpose of ensuring good wettability of the solder on the bonding pads. Finally, the circuit electrodes are retrieved using water soluble tape for aligned transfer to the device substrate.

Integration Plan

A number of issues need to be addressed when integrating the various components of the closed-loop wearable devices described above. These issues will be discussed below.

Typically, as seen in other miniature lab-on-a-chip type sensors, microfluidics and syringe pumps are used to facilitate the transfer of the test solution to the sensor and to flush out the sensor after each measurement. However, these tools are much too large and bulky for completely wearable devices meant for use outside of a laboratory and as a completely self-contained sensor. Instead, the more promising solution is to use paper microfluidics, which is much more amenable to flexible systems. The paper microfluidics serve as a fluidic plumbing system handles transferring sweat from the epidermis to the sensing area for a limited amount of time and then removing it so that old sweat does not interfere with new measurements.

Figure 16:
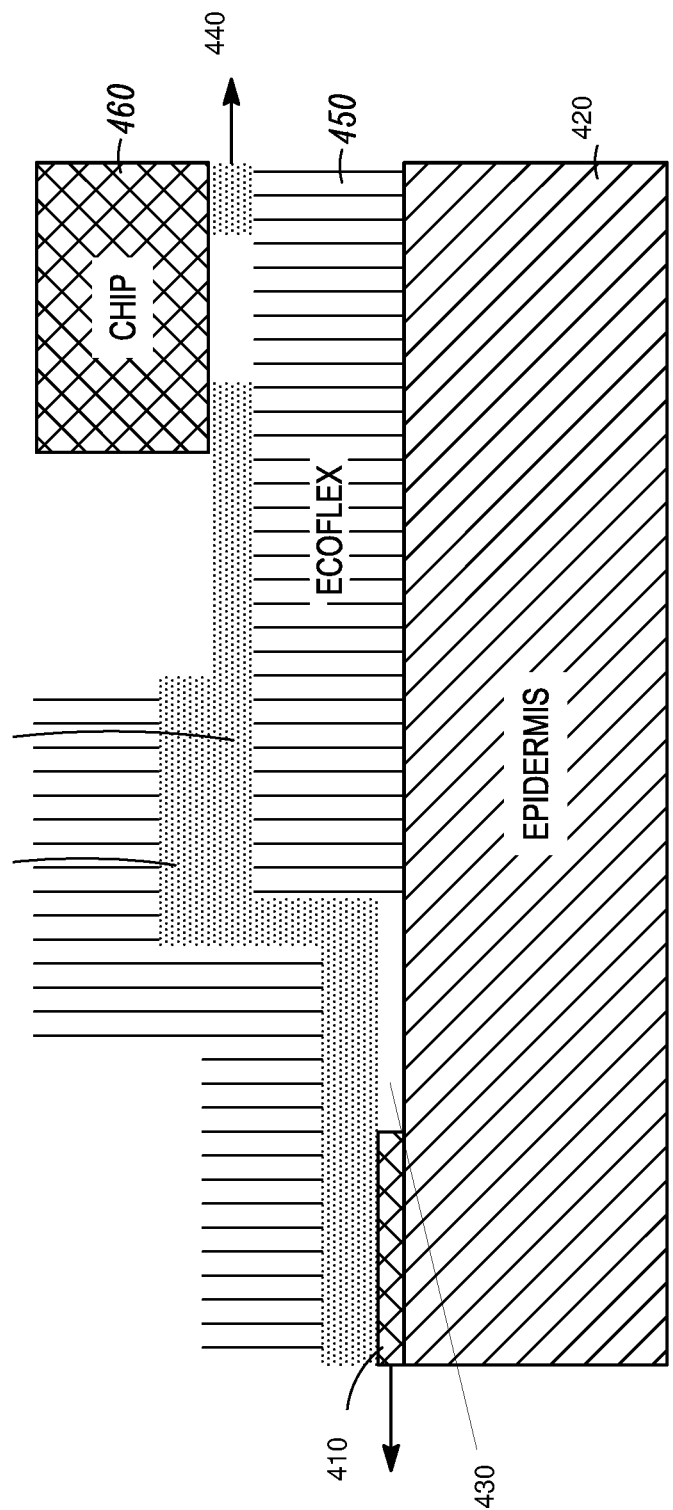
FIG. 16 shows a cross-sectional view through a portion of a closed-loop wearable platform that is taken through one of the biosensors.

Nitrocellulose-based polymers use capillary wicking to pull the fluid onto the sensor thus avoiding the use of bulky pumps. FIG. 16 shows a cross-sectional view through a portion of the closed-loop wearable platform 100 that is taken through one of the biosensors. A passivation layer 410 is shown in contact with the epidermis 420 of a patient. The passivation layer 410 is formed from a porous and inert material such as an elastomer silicone material that absorbs sweat into its pores. A fluidics layer 430 is located between the sensor electrodes 440 and the passivation layer 410. In some cases the fluidics layer 430 may be formed from the same material as the passivation layer 410. However, the fluidics layer 430 includes laterally extending channels that can guide the sweat received from the passivation layer 410 to distribute it laterally among different types of sensors. At the end of the nitrocellulose-based polymer a superabsorbent polymer, such as is found in diapers, may be provided, to serve as a bulk reservoir for measured sweat. This arrangement is similar to those used in home-based pregnancy tests, except that in the wearable platform the testing is continuous, rather than single use as in a pregnancy test. From preliminary calculations, it is estimated that a 1 $cm^2$ sensing area and similarly sized reservoir can store up to three days of sweat under normal conditions and at least eight hours under heavy exercise. In applications such as smart band-aids where redressing of a wound needs to be done frequently, the estimated reservoir size is more than enough to last for the lifetime of the sensors. Furthermore, the entire patch could be encapsulated in a bandage like material to ensure contact with the skin and isolation from outside contaminants.

Another integration issue that needs to be addressed concerns the overall power budget of the closed-loop wearable platform. The power source for wearable electronic devices is a challenging problem. In the short term, the overall power consumption of the system can be reduced by lowering the duty cycle of the control system, and memory can be added for local data storage if necessary.

Yet another integration-related issue concerns the independent testing of the individual sensing and actuating components after they have been integrated on the platform. This may be accomplished by feeding emulated physiological signals generated by a signal generator to the components to determine if they operating properly. The information gained in this way can provide valuable information concerning, for instance, characteristics of the input signal provided to the actuators and the frequency of the actuator upon real physiological signals in contrast to emulated signals. In this way direct confirmation of the operation of each individual component can be obtained, which also provides a relatively easy for debugging if any errors occur at a later stage. The ultimate demonstration of autonomous actuation and wireless sensing (if this function is provided) can be performed when all detailed verifications of individual components are completed. Test measurements may be obtained over a time period of several days to a week. Multiple wearable devices may be tested simultaneously for the target time period. As the target period is relatively short it is unnecessary to perform long-term (e.g., several weeks) testing in an accelerated environment (e.g., in a temperature/humidity environmental chamber).

Yet another integration-related issue concerns the air permeability of the porous elastomers or other elastically stretchable materials that are employed. Because the human body is constantly evaporating moisture/sweat to the environment, the substrates and packaging materials used in the closed-loop wearable platform should be microporous so that moisture evaporation is not prevented during long term use. Therefore, the porous elastomers that are employed (e.g., silicone elastomer) should be made nano/microporous for this purpose. This can be accomplished by fabricating bicontinuous nanostructures in polymer matrices using block copolymer assisted microphase separation, and nano/microporous channels can be opened by selective etching/dissolving of one phase. For instance, mixtures of PDMS, PMMA and PDMS-b-PMMA precursors can be selectively etched to produce bicontinuous PDMS thin films with similar mechanical properties to bulk PDMS. By tuning the reaction conditions and precursor chemistry, the size, size distribution, and morphology of the ion channels can be controlled. Submicron pores are needed to provide ion migration channels without electrical shortage. Therefore, complex bicontinuous structures may be preferred over structures with oriented geometries.

Generally, the integration of discrete components into a soft wearable system may be viewed as a packaging process. As the price of ICs continues to drop, packaging takes up a great amount of the total cost of the system. Also, because the devices may be disposable, device fabrication costs for a macroscale process should ideally be reduced. Manufacturing costs can be lowered by batch processing and by using process innovations such as the use of screen printing versus lithography and etching. In addition, the use electrodeposition techniques instead of vacuum deposition methods may further reduce the manufacturing steps that are needed and improve throughput.

One of the challenges involved in developing a wearable device for long-term health monitoring concerns the ability of the platform to remain on the skin for more than a few days. Once a wearable device is mounted on the epidermis by van der Waals forces alone, it starts to show delamination from the skin after about 1 day due to exfoliation of dead cells. Therefore, additional strategies are needed to keep the wearable platform in contact with the skin when it is to be worn over a long term to e.g., continuously monitor electrophysiological signals on the skin. Also, since the active materials used to fabricate the wearable sensors or actuators are mainly functional semiconductors and metals, washing may remove or damage the structure of the materials. Sweat, which is slightly acidic, may also affect their performance. Therefore, for long term wear, these devices should be able to tolerate daily damage, such as laundering and abrasion. This issue may be addressed by using medically proven skin products such as spray-on-bandages that are a blend of an acrylate terpolymer and a polyphenylmethylsiloxane with hexamethyldisiloxane as a volatile solvent. This polymer is available in a spray can and can yield a thin, solid conformal and transparent coating (about 1 µm thick) on skin upon evaporation. These films provide hydrophobic waterproof surfaces on the skin that block water, dirt and other debris, but offer sufficient levels of breathability to avoid adverse effects on the skin while wearing for a few days or a week.

Wireless Communication

The actuators in the closed-loop wearable devices are trigged by the control system, which drives the actuators on the basis of the signals from the sensors. While in the examples discussed above this control system unit is located on the wearable device itself in the form of a control system, in some cases some of the functionality of this control system may be performed by a processing unit located elsewhere. For this purpose the wearable device may wirelessly communicate with a mobile computing device that is in close proximity to the patient and preferably carried by the patient. One example of such a mobile computing device is a mobile phone such as a cell phone (e.g., a smart phone).

Additionally, some patients may require the use of multiple wearable devices that are distributed over their body for concurrent monitoring of spatially diverse clinical signals and/or different human body signals. In this case all of the wearable devices may wirelessly communicate with the mobile computing device to form a body area network (BAN) that can be under the control of the mobile computing device, which acts as a central processing master unit on the body.

The mobile computing device is useful not only to coordinate among different wearable devices, but also because wearable device technology in the near future will most likely lack the capability to build high performance central processing units on the device itself or to send a signal over a long distance. While cell phone ownership is rising rapidly, access to traditional health care and providers is often limited, particularly in developing countries. Therefore, cell phones are one potential avenue for the delivery of health management strategies by interfacing them with the passive sensors and active physical treatment functions. In this regard, cell phones can be transformed into portable healthcare tools through the use of intrinsic and external additionally developed software. In reality, the enormous potential for cell phones as enabling technologies to transform remote healthcare, personal health data management, and basic health research has led to the rapid development of numerous health-related phone applications and device attachments, which aim to improve health by influence behaviors, such as eating and exercise patterns, and risk-related behavior.

The sensors in the wearable device can continuously monitor vital parameters, and transfer the acquired data wirelessly to the cell phone where the data are local stored and analyzed for user feedback, and, if necessary, transmit to professional medical services. The data may be wirelessly transmitted continuously as it is received, or to conserve power, it may be transmitted intermittently, perhaps on a periodic basis. The wearable device will only need to transmit over a relatively short distance (e.g., one meter) using, for instance, a communication protocol such as near-field communications (NFC) or Bluetooth®. The control system 360 shown in the illustrative wearable device of FIG. 7, for example, includes an NFC antenna coil 373. The computing device may automatically process the monitored parameters it receives, analyze patient status, estimate trends, detect any impending deviations from normal and send system reactions messages (e.g., therapy recommendations such as suggesting electrotherapy or drug delivery) to the actuators or automatically contact medical help in case of an emergency.

By providing 24/7 continuous monitoring health status data to a central information system, machine learning algorithms may be utilized to provide decision support or diagnosis assistance. For instance, the measured data may be analyzed statistically, which may provide better robustness and reliability. In this way the management and treatment of diseases could become a highly information-rich process. As this data set grows, differences between different types of certain diseases (e.g. seizures, stroke) may be determined more accurately and provide deeper insights into their causes and outcomes, perhaps even to the point of being able to predict an impending episode. It may also allow for treatments that are tailored more carefully to a person's specific form of disease. In this way, mobile computing devices such as cell phones not only have the ability to facilitate communication between individuals and health care providers, but can also be used to collect data that drives personal decision making.

Continuous diagnoses by several sensors are more likely to accurately detect symptoms of an illness compared to a single measurement. In addition, because the wearable devices offer robust, non-irritating skin/electrode contact, they are likely the most natural and unbiased settings for authentic and outlier-free data of internal human body signals. These devices may thus provide an enhanced (e.g., more accurate and less restrictive) method of acquiring bioelectrical signals from the body, while also providing timely intervention in emergency situations.

Long Term Wearability

One challenge in producing a wearable device is its wearability on the skin for more than a few days for long-term health monitoring. Once a wearable device is mounted on the epidermis by van der Waals forces alone, it starts to show delamination from the skin after about one day due to exfoliation of dead cells. Therefore, additional strategies to maintain contact between the device and the skin is required when the device is to be worn for longer periods of time. Also, since the active materials used to fabricate the wearable sensors or actuators are mainly functional semiconductors and metals, washing may remove or damage the structure of the materials. Sweat, which is slightly acidic, may also affect their performance. Therefore, for wearing long term, these devices should be designed to tolerate daily damage, such as laundering and abrasion. This issue may be addressed by utilization of medically proven skin products such as spray-on-bandages that are a blend of an acrylate terpolymer and a polyphenylmethylsiloxane with hexamethyldisiloxane as a volatile solvent. When this polymer is provided in a spray can, it yields a thin, solid conformal and transparent coating (about 1 μm-thick) on skin upon evaporation. These films provide hydrophobic waterproof surfaces on the skin that block water, dirt and other debris, but offer sufficient levels of breathability to avoid adverse effects on the skin during wearing for a few days or a week.

Device Passivation

When producing an implantable electronic device biocompatibility should be taken into account. Once implanted into the body, a fibrous, collagen-based membrane can develop around the device. An implanted device should have a package that is biocompatible. The surface properties of the polymer film may be selectively tuned by the incorporation of functionalized elements to meet specific requirements. The coated polymer may be biocompatible with the surrounding cells so as not to induce any toxic side effects.

EM Decoupling From Human Body Absorption

The human body is a strong absorber of electromagnetic (EM) waves. If the wearable device is able to wirelessly communicate with an external device, the working distance of the antenna located on the wearable device can be increased by decoupling it from human body absorption. Stretchable antennas and their coupling to the external receiving antenna can be simulated using FEA software, HFSS, with dielectrics properties of the human body of the IFAC-CNR. As the overall dielectric properties of the human body are a function of its surface areas, fine tuning of the transponder antenna can be achieved by either inserting an elastomer spacer between the coil and skin, shifting the resonance upwards and diminishing resistive losses due to the human body, or adding a high permittivity superstrate to shift the resonance downwards. Impact of the deformations (bending, stretching, and compression) on the antenna behavior should also be examined.

Power Consumption Requirements

A wearable electronic system is made up of different components, each of which generally fall in one of the following categories: sensing, communication and data processing, actuation, and energy. The power source for wearable electronics is a challenging problem. In the short term, the overall power consumption of the system can be reduced by lowering the duty cycle of the radio systems, and memory can be added for local data storage.

Cost and Throughput

The integration of discrete components into a soft system is to a large extent a packaging process. As the price of integrated circuits ("chips") continues to drop, packaging takes up a greater amount of the total cost of the system. Also, device fabrication costs for a macroscale process should be reduced because the device may be disposable. It is therefore important for this technology to be cost-effective. The manufacturing cost can be lowered by batch processing. Process innovations such as the use of screen printing vs. lithography and etching, electrodeposition vs. vacuum deposition methods may further reduce the manufacturing steps needed and improve throughput.

Fabrication instruments include hood, autoclave, spin coater, hotplate, electron beam evaporator, plasma enhanced chemical vapor deposition, electrochemical station, desktop sputter coater, mask aligner, reactive ion etcher, optical microscope, furnaces (convection, vacuum, UV ozone), glove box, DI water generator, sonicator, centrifuge, balance, consumables (gold, SOI wafers, polyimide precursors, etc).

Measurement instruments include UV laser and lens systems, air table, solar station, probe station, four point surface conductivity analyzer, Keithley I-V measurement setup, pulsed high voltage source, synthesized function generator, current preamplifier, voltage amplifier, linear motor to apply mechanical strain, pH meter, dissolved oxygen analyzer, oscilloscope, board antenna, band pass filter, low noise amplifier, frequency counter, stretcher, strain-stress analyzer.

Device Testing

As part of the fabrication process, mechanical and electrical testing of the wearable devices may be performed after they are assembled. Mechanical testing may be accomplished by depositing an array of metal dots through a polyimide shadow mask mounted on the back side of the wearable device. Equal-biaxial stretching may then be applied to the device using a mechanical stage that can gradually add/remove strain simultaneously in both directions. Images of the device at various stages of deformation can be collected from the backside the device so that the metal dots are clearly visible. The Young's moduli of the devices with and without the chips and interconnect network may be measured in orthogonal directions. The strain-stress curves can then be averaged over at least three individual measurements. Mechanical simulations may also be performed, using, for instance, FEA techniques.

Electrical testing of the wearable devices can be accomplished by placing the assembled wearable device on the skin after removing any hair on the skin epidermis and cleaning it with a pad soaked in alcohol. Afterwards, the device/ultrathin silicone membrane/PVA tri-layer structure is placed on the preferred areas on the skin for recording. By adding water onto the water soluble PVA, the PVA tape is removed and only the device backed up by the ultrathin silicone membrane remains on the skin by van der Waals forces.

For resonant inductive coupling, alternating current is generated in the secondary coil (which includes an LC oscillator) of the device by applying alternating current to a primary coil that is in proximity (within mm's) to the secondary coil. The alternating current in the secondary coil is converted into a direct current output by a Schottky diode rectifier and an integration capacitor. The direct current activates the entire device. Additional capacitors remove high frequency and DC components of the electrophysiological signals collected, with a floating ground. A voltage controlled RF oscillator transforms the amplified data into an FM RF signal at ~2.4 GHz that passes out of the device through a compact three-dimensional antenna. A separate patch antenna, RF amplifier and frequency counter can receive the transmitted RF reliably at a distance of up to 1 m, when operated in a room designed to eliminate background electrical noise. The varactor mixing is visualized at the external board antenna through a spectrum analyzer for measuring spectral content and/or demodulator to view original baseband electrophysiological signal temporal waveform.

When testing the wearable device on an individual, the individual is to sit still and remain quiet. To acquire electrocardiogram (ECG) signals, the wearable device is placed on the lower-left edge of the rib cage, near the left side of the midline of the chest. The expected behavior includes high frequency oscillations with amplitudes between about 0.5 to 1 $mV_{pp}$. A single bi-polar ECG channel can be measured from standard commercial adhesive electrodes fastened e.g., 7 cm apart, on either side of the sternum in the 4th intercostal space, corresponding to ECG channels V1 and V2. The wearable device is fastened directly under the standard electrodes, with the two electrodes at the same distance as the commercial adhesives. The commercial system incorporates a ground electrode attached to a more proximal section of the right arm. The wireless system utilizes a floating ground.

The high-frequency electromyogram (EMG) activity from the forearm can be acquired, again to compare the commercial and wearable systems. A bi-polar EMG electrode pair can be placed on the proximal left forearm over the flexor carpi radialis muscle. For commercial recording a pair of Ag/AgCl ring electrodes can be used, fixed with an adhesive sticker to the skin along with conductive electrode paste, with a nearby ground. Directly parallel with these the wearable system and electrodes are placed such that the distance between the electrodes and the angle with respect to the muscle is the same. The individual places his/her palm on the underside of a desk and flexes the forearm, as if to clench their hand but with no hand movement. The individuals then relax their arm, and repeat this rhythmically roughly every few (e.g., two) seconds.

For EOG, bi-polar commercial adhesive electrodes are centered above and below and medial of the individual's left eye, again about 7 cm apart (and slightly lateral from the left outer canthus). The wearable system and the electrodes are placed directly lateral to, and parallel with the commercial system. The individual begins by quickly blinking their eyes, and then blinking every second or so until the recording ends.

For EEG, a pair of EEG electrodes may be affixed to the forehead. A pair of Ag/AgCl electrodes are placed along the hairline, with the electrode at roughly position Fpz in the center referenced to the lateral electrode at location AF8. The flexible electrodes are placed directly inferior, parallel, and the same distance apart. The individual begins with a minute of mental math, counting backwards by e.g., 7 from e.g., 200. They then close their eyes and rest for another minute.

The sensing and actuating components of the integrated devices can be tested independently. The emulated physiological signals generated by a signal generator can be fed into the wearable actuator to see if the actuator is working in principle with an appropriate sensitivity. This test can provide valuable information concerning the input signal amplitude and frequency of the actuator upon real physiological signals, in contrast to emulated signals. This approach offers direct confirmation of each individual component and is also easier for debugging if anything goes wrong at a later stage. The ultimate demonstration of the wireless sensing and autonomous actuation functions can be performed after all the detailed verifications of the individual components have been completed. The wirelessly acquired signals may be characterized for their signal integrity as well as robustness over time. The main target period of the measurements may be several days to a week. Multiple wearable devices can be simultaneously tested over the target period. As the target period is relatively short it will generally be unnecessary to perform long-term (multiple weeks or more) testing in an accelerated environment (i.e., in a temperature/humidity environmental chamber).

Regarding mechanical analysis, a full 3D finite element analysis (FEA) may be used to analyze the post-buckling behavior of the entire device under uniaxial and biaxial stretching. The chips can be selectively bonded to the silicone substrate via small circular and rectangular pedestals. Each of the metal interconnect lines can be encased, top and bottom, by a thin layer of polyimide. In one example, the elastic modulus (E) and Poisson's ratio (v) were found to be $E_{Ecoflex}=0.0623$ MPa and $v_{Ecoflex}=0.49$ for Ecoflex; $E_{Cu}=119$ GPa and $v_{Cu}=0.34$ for copper; and $E_{PI}=2.5$ GPa and $v_{PI}=0.34$ for PI. Eight-node 3D solid elements and four-node shell elements can be used for the Ecoflex and self-similar electrode, respectively, and refined meshes may be adopted to ensure accuracy. Linear buckling analyses may be carried out to determine the critical buckling strain and the lowest buckling mode for each interconnect, which are then implemented as initial geometric imperfections in the postbuckling simulation. The evolution of deformed configurations with applied strains can be obtained from FEA for the entire device under both uniaxial and biaxial stretchings.

Regarding electrical analysis, a separate patch antenna, RF amplifier and frequency counter can receive the transmitted RF reliably at a distance of up to about one meter. Laminating the wearable device across the sternum with each electrode in bi-lateral fourth intercostal spaces enables the collection of ECG data. Measurements, with clearly identifiable QRS complexes, should be expected. To determine the effectiveness and reliability of the epidermal RF system, the data from the wearable device can be compared to data obtained from a standard electrophysiological recording amplifier and digital recorder using standard commercial adhesive electrodes fastened to the distal, palmer surface of the bilateral wrists, using the right wrist as a reference for the left. These recording locations correspond to standard left arm and right arm extremity electrodes in a clinical ECG. The voltage difference between wrists can be simultaneously amplified, filtered, digitized, and wirelessly recorded by the wearable device (e.g., 1000 Hz; DC–500 Hz bandwidth after online filter; bit depth 10 µV) and by a commercial electrophysiology system (e.g., BrainVision Brainamp MR Plus; 1000 Hz; DC–250 Hz bandwidth after online filter; bit depth 0.01 µV).

The voltage difference between V1 and V2 is simultaneously amplified, filtered, digitized, and recorded by the wireless epidermal system, and by a commercial electrophysiology system. The commercial system may incorporate a ground electrode attached to a more proximal section of the right arm. The wireless system can use a floating ground. Offline, data are filtered with a band pass between 0.5 and 20 Hz to remove line noise and other high frequency artifacts, as well as slow drifts in the signal. The mean voltage of each signal may be subtracted to remove DC offset differences. The data are then normalized to remove the influence of electrode impedance differences between the commercial and flexible systems. Frequency spectra of the ECG traces is computed with a fast Fourier transformation (FFT) of the entire time series. The smaller peaks represent harmonics of the heart rate. The integrity and sensitivity of the acquired temporal waveform in terms of the peaks and QRS complex can be examined. Correspondence is made between the commercially and wireless recorded ECG spectra as well. Electric potentials of heart activity seen as an electric equivalent generator can be measured by surface electrodes on the chest. These measurements provide very low voltage amplitudes (~1 mV for R-wave) due to the resistance of the thoracic medium and skin contact. A complete cardiograph waveform provides detailed insight into the ventricle functions, e.g., the P, Q, R, S and T waves as well as the various inter-wave timings. The R-wave is usually counted over time to derive the heart rate (HR) per second. Besides the RR-timing (HR=1/RR), the heart rate variability (HRV) is a relevant health status indication, e.g., for the estimation of stress level.

The same amplifier settings for EMG are used as in the ECG analysis; here the ground is affixed, for the commercial system to the left outer forearm. Offline, data are filtered with a band-pass from 100-300 Hz to isolate high-frequency muscle activity. The mean voltage of each signal is subtracted to remove DC offset differences. The data are then normalized to remove the influence of electrode impedance differences between the commercial and flexible systems, and then rectified for illustration.

For EOG, the amplifier settings can be identical except that an electrode on the individual's left forearm may act as a ground for the commercial system. Offline, data can be filtered with a band-pass from 0.1 and 30 Hz to remove high frequency muscle activity and low-frequency drifts. The mean voltage of each signal may be subtracted to remove DC offset differences. The data may then be normalized to remove the influence of electrode impedance differences between the commercial and flexible systems.

For EEG, offline, data can be filtered with a band-pass from 1-30 Hz to remove high frequency muscle activity and low-frequency drifts. The mean voltage of each signal can be subtracted to remove DC offset differences. The data may then be normalized to remove the influence of electrode impedance differences between the commercial and flexible systems. A time-frequency transform of the EEG data from the forehead may be computed with a wavelet decomposition. During mental math, an increase in high-frequency activity between 12-30 Hz (Beta band) is expected to be observed that dissipates during rest. Spectra during rest are expected to show a clear peak in the alpha band at 11 Hz that is larger than during math. Fast Fourier transform can be performed to reveal the high-frequency activity during mental math, and more low-frequency activity during rest.

While exemplary embodiments and particular applications of this invention have been shown and described, it is apparent that many other modifications and applications of this invention are possible without departing from the inventive concepts herein disclosed.

The invention claimed is:

1. A wearable medical device, comprising:
   a first elastically stretchable or flexible substrate that is removably attachable to an epidermis of a user by van der Waals forces alone;
   at least one biosensor located on the substrate for measuring at least one physiological parameter or vital sign of the user while the substrate is attached to the user;
   at least one actuator located on the substrate for delivering at least one action to the user while the substrate is attached to the user;
   a stretchable microcontroller circuit mounted on the substrate, the stretchable microcontroller circuit being operatively associated with the at least one biosensor and the at least one actuator such that the at least one actuator, responsive to a control signal received from the stretchable microcontroller circuit, delivers at least one action to the user in a closed-loop manner without any external intervention based at least in part data received by the stretchable microcontroller circuit from the at least one biosensor, the stretchable microcontroller circuit being releasably connectable to the at least one biosensor and the at least one actuator, wherein the stretchable microcontroller circuit is encapsulated in a containment chamber having a liquid material therein for reducing strain, the stretchable microcontroller circuit being configured to distinguish between normal and abnormal levels of the at least one physiological parameter of the user and to cause the at least one actuator to be active when an abnormal level of the at least one physiological parameter is detected; and
   electrical interconnects each having a self-similar serpentine configuration and electrically interconnecting the at least one biosensor, the at least one actuator and the stretchable microcontroller circuit such that the at least one biosensor, the at least one actuator and the stretchable microcontroller circuit define a common stretchable or flexible package that is able to directly adhere to skin via van der Waals forces alone and is able to naturally deform with the skin.

2. The wearable medical device of claim 1 wherein the at least one actuator is selected from the group consisting of a drug delivery system, a thermal actuator, an electrical actuator, a mechanical vibrator, a light activator, and a pressure actuator.

3. The wearable medical device of claim 1 wherein the at least one actuator includes a drug delivery device.

4. The wearable medical device of claim 3 wherein the drug delivery device includes a transdermal drug delivery system (TDDS).

5. The wearable medical device of claim 4 wherein the TDDS includes at least one microneedle for puncturing a stratum corneum layer of skin.

6. The wearable medical device of claim 5 wherein the TDDS further includes a micro-heater for causing a drug or other agent to be expelled from the microneedle.

7. The wearable medical device of claim 6 wherein the TDDS further includes a thermos-responsive expandable layer that expands upon application of heat from the micro-heater.

8. The wearable medical device of claim 1 wherein the at least one biosensor includes an electrochemical sensor.

9. The wearable medical device of claim 1 wherein the at least one biosensor includes a temperature sensor.

10. The wearable medical device of claim 1 wherein the at least one biosensor includes a biosensor array module having a plurality of biosensors that are located on a second elastically stretchable substrate that is removably attachable to the first elastically stretchable substrate.

11. The wearable medical device of claim 10 wherein the biosensor array module further comprises at least one electrically conductive bonding pad and electrical interconnects electrically interconnecting the biosensors to the bonding pad, the electrical interconnects each having a self-similar serpentine configuration.

12. The wearable medical device of claim 1 wherein the at least one actuator includes an actuator array module having a plurality of actuators that are located on a second elastically stretchable substrate that is removably attachable to the first elastically stretchable substrate.

13. The wearable medical device of claim 12 wherein the actuator array module further comprises at least one electrically conductive bonding pad and electrical interconnects electrically interconnecting the actuators to the bonding pad, the electrical interconnects each having a self-similar serpentine configuration.

14. The wearable medical device of claim 1 wherein the elastically stretchable substrate includes a silicone elastomer material.

15. The wearable medical device of claim 1 wherein the common stretchable or flexible package has an elastic modulus no more than 3-5% higher than an elastic modulus of the first elastically stretchable or flexible substrate.

16. The wearable medical device of claim 1 wherein the common stretchable or flexible package has an elastic modulus matching that of human skin.

* * * * *